(12) United States Patent
Wang

(10) Patent No.: US 10,507,199 B2
(45) Date of Patent: Dec. 17, 2019

(54) MOLECULES IN THE TRYPTOPHAN-5-HYDROXYTRYPTOPHAN-SEROTONIN-NAS-MELATONIN/6-HYDROXYMELATONIN SULFATE-MELATONIN RECEPTOR 1A PATHWAY IN NEUROLOGICAL DISEASES

(71) Applicant: The Brigham and Women's Hospital, Inc., Boston, MA (US)

(72) Inventor: Xin Wang, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 15/974,184

(22) Filed: May 8, 2018

(65) Prior Publication Data

US 2018/0318258 A1 Nov. 8, 2018

Related U.S. Application Data

(60) Provisional application No. 62/502,827, filed on May 8, 2017.

(51) Int. Cl.
| | |
|---|---|
| *A61K 31/4045* | (2006.01) |
| *A61P 9/10* | (2006.01) |
| *G01N 33/493* | (2006.01) |
| *G01N 33/74* | (2006.01) |
| *A61K 41/00* | (2006.01) |
| *G01N 33/50* | (2006.01) |
| *G01N 33/94* | (2006.01) |

(52) U.S. Cl.
CPC ...... *A61K 31/4045* (2013.01); *A61K 41/0052* (2013.01); *A61P 9/10* (2018.01); *G01N 33/493* (2013.01); *G01N 33/5091* (2013.01); *G01N 33/74* (2013.01); *G01N 33/942* (2013.01); *G01N 2333/70571* (2013.01); *G01N 2800/28* (2013.01); *G01N 2800/2871* (2013.01); *G01N 2800/52* (2013.01); *G01N 2800/7038* (2013.01)

(58) Field of Classification Search
CPC ........... A61K 31/4045; A61K 41/0052; G01N 33/00; G01N 2800/2871; G01N 33/493; G01N 33/74; A61P 9/10
See application file for complete search history.

(56) References Cited

U.S. PATENT DOCUMENTS

2015/0258064 A1* 9/2015 Raschini ............ A61K 31/4045
                                                    514/415

OTHER PUBLICATIONS

Kovács J, Brodner W, Kirchlechner V, Arif T, Waldhauser F. Measurement of urinary melatonin: a useful tool for monitoring serum melatonin after its oral administration. J Clin Endocrinol Metab. Feb. 2000;85(2):666-70. PubMed PMID: 10690873. (Year: 2000).*
Adi et al., "Melatonin mtl and mt2 receptor expression in Parkinson's disease," Med Sci Monit, 2010, 16:BR61-67.
Alonso-Alconada et al., "Neuroprotective effect of melatonin: A novel therapy against perinatal hypoxia-ischemia," Int J Mol Sci, 2013, 14:9379-9395.
Aly et al., "Melatonin use for neuroprotection in perinatal asphyxia: A randomized controlled pilot study," J Perinatol, 2015, 35:186-191.
Andrabi et al., "Direct inhibition of the mitochondrial permeability transition pore: A possible mechanism responsible for anti-apoptotic effects of melatonin," FASEB J, 2004, 18:869-871.
Bartley et al., "Brdu-positive cells in the neonatal mouse hippocampus following hypoxic-ischemic brain injury," BMC Neurosci, 2005, 6:15.
Belaid et al., "Effect of melatonin on sleep disorders in a monkey model of Parkinson's disease," Sleep Med, 2015, 16:1245-1251.
Cardinali et al., "Clinical aspects of melatonin intervention in Alzheimer's disease progression," Curr Neuropharmacol, 2010, 8:218-227.
Carloni et al., "Melatonin modulates neonatal brain inflammation through endoplasmic reticulum stress, autophagy, and mir-34a/silent information regulator 1 pathway," J Pineal Res, 2016, 61:370-380.
Carloni et al., "Melatonin protects from the long-term consequences of a neonatal hypoxic-ischemic brain injury in rats," J Pineal Res, 2008, 44:157-164.
Cetinkaya et al., "Possible neuroprotective effects of magnesium sulfate and melatonin as both pre- and post-treatment in a neonatal hypoxic-ischemic rat model," Neonatology, 2011, 99:302-310.
Chen et al., "Melatonin enhances the hypoxic response of rat carotid body chemoreceptor," J Pineal Res, 2005, 38:157-163.
Chern et al., "Melatonin ameliorates neural function by promoting endogenous neurogenesis through the MT2 melatonin receptor in ischemic-stroke mice," Free Radic Biol Med, 2012, 52:1634-1647.
Cheung et al., "Preclinical evaluation of pharmacokinetics and safety of melatonin in propylene glycol for intravenous administration," J Pineal Res, 2006, 41:337-343.
Correa et al., "Expression of the melatonin receptor and tryptophan hydroxylase in placentas of the fetus with intra-uterine stress," Eur J Obstet Gynecol Reprod Biol, 2009, 147:234-236.
Cotten and Shankaran, "Hypothermia for hypoxic-ischemic encephalopathy," Exp Rev Obstet & Gynec, 2010, 5:227-239.
Dubocovich et al., "International union of basic and clinical pharmacology. Lxxv. Nomenclature, classification, and pharmacology of g protein-coupled melatonin receptors," Pharmacol Rev, 2010, 62:343-380.
Dubocovich and Markowska, "Functional mtl and mt2 melatonin receptors in mammals," Endocrine, 2005, 27:101-110.

(Continued)

*Primary Examiner* — Theodore R. West
(74) *Attorney, Agent, or Firm* — Fish & Richardson P.C.

(57) ABSTRACT

Methods that include determining levels of melatonin pathway agents (melatonin, L-tryptophan, 5-hydroxytryptophan (5-HTP), serotonin, N-acetylserotonin (NAS), and melatonin receptor 1A (MT1)) in Hypoxic-ischemic brain injury in both newborns (HIE) and adults (stroke), and in ALS, and optionally administering these agents to treat these conditions.

12 Claims, 22 Drawing Sheets
(20 of 22 Drawing Sheet(s) Filed in Color)

(56) References Cited

OTHER PUBLICATIONS

Gitto et al., "Increased levels of malondialdehyde and nitrite/nitrate in the blood of asphyxiated newborns," J Pineal Res, 2001, 31:343-349.
Gitto et al., "Oxidative stress of the newborn in the pre- and postnatal period and the clinical utility of melatonin," J Pineal Res, 2009, 46:128-139.
Han et al., "Bdnf blocks caspase-3 activation in neonatal hypoxia-ischemia," Neurobiol Dis, 2000, 7:38-53.
Holtzman et al., "Nerve growth factor protects the neonatal brain against hypoxic-ischemic injury," Ann Neurol, 1996, 39:114-122.
Husson et al. Melatoninergic neuroprotection of the murine periventricular white matter against neonatal excitotoxic challenge. Ann Neurol. 2002;51:82-92.
Jacob et al., "Melatonin as a candidate compound for neuroprotection in amyotrophic lateral sclerosis (als): High tolerability of daily oral melatonin administration in als patients," J Pineal Res, 2002 33:186-187.
Jahani-Asl et al., "Mitofusin 2 protects cerebellar granule neurons against injury-induced cell death," J Biol Chem, 2007, 282:23788-23798.
Kilic et al., "Melatonin reduces disseminate neuronal death after mild focal ischemia in mice via inhibition of caspase-3 and is suitable as an add-on treatment to tissue-plasminogen activator," J Pineal Res, 2004, 36:171-176.
Kilic et al., "Evidence that membrane-bound G protein-coupled melatonin receptors MT1 and MT2 are not involved in the neuroprotective effects of melatonin in focal cerebral ischemia," J Pineal Res, 2012, 52:228-235.
Lacoste et al., "Anatomical and cellular localization of MT1 and MT2 receptors in the adult rat brain," J Pineal Res, 2015, 58:397-417.
Lee et al. "Melatonin's protective action against ischemic neuronal damage is associated with up-regulation of the MT2 melatonin receptor," J Neurosci Res, 2010, 88:2630-2640.
Lin et al., "Melatonin attenuates traumatic brain injury-induced inflammation: a possible role of mitophagy," J Pineal Res, 2016, 61:177-186.
Lopez-Gonzalez et al., "Melatonin treatment improves primary progressive multiple sclerosis: a case report," J Pineal Res, 2015, 58:173-177.
Ma et al., "Therapeutic hypothermia as a neuroprotective strategy in neonatal hypoxic-ischemic brain injury and traumatic brain injury," Curr Mol Med, 2012, 12:1282-1296.
Mahle and Watson, "Melatonin receptors: Potential targets for central nervous system disorders," Exp Opin Investig Drugs, 1997, 6:399-406.
Manchester et al., "Melatonin: an ancient molecule that makes oxygen metabolically tolerable," J Pineal Res, 2015, 59:403-419.
Manev et al., "Increased brain damage after stroke or excitotoxic seizures in melatonin-deficient rats," FASEB J, 1996, 10:1546-1551.
Marret et al., "Effect of ibotenate on brain development: An excitotoxic mouse model of microgyria and posthypoxic-like lesions," J Neuropathol Exp Neurol, 1995, 54:358-370.
Martin et al., "Melatonin but not vitamins C and E maintains glutathione homeostasis in t-butyl hydroperoxide-induced mitochondrial oxidative stress," FASEB J, 2000, 14:1677-1679.
McDonald et al., "Mk-801 protects the neonatal brain from hypoxic-ischemic damage," Eur J Pharmacol, 1987, 140:359-361.
McLean and Ferriero, "Mechanisms of hypoxic-ischemic injury in the term infant," Semin Perinatol, 2004, 28:425-432.
Morgan et al., "Melatonin receptors: Localization, molecular pharmacology and physiological significance," Neurochem Int, 1994, 24:101-146.
Muller et al., "17beta-estradiol protects 7-day old rats from acute brain injury and reduces the number of apoptotic cells," Reprod Sci, 2013, 20:253-261.
Musshoff et al., "Melatonin receptors in rat hippocampus: Molecular and functional investigations," Hippocampus, 2002, 12:165-173.
Olegario et al., "Pulmonary innate immune response and melatonin receptors in the perinatal stress," Clin Dev Immunol, 2013, 2013:340959.
Parada et al., "Neuroprotective effect of melatonin against ischemia is partially mediated by alpha-7 nicotinic receptor modulation and ho-1 overexpression," J Pineal Res, 2014, 56:204-212.
Pei et al., "Melatonin reduces nitric oxide level during ischemia but not blood-brain barrier breakdown during reperfusion in a rat middle cerebral artery occlusion stroke model," J Pineal Res, 2003, 34:110-118.
Peters et al., "Modulation of intercellular calcium signaling by melatonin in avian and mammalian astrocytes is brain region-specific," J Compar Neurol, 2005, 493:370-380.
Reiter et al., "Melatonin and its relation to the immune system and inflammation," Ann NY Acad Sci, 2000, 917:376-386.
Reiter et al., "Melatonin as an antioxidant: under promises but over delivers," J Pineal Res, 2016, 61:253-278.
Rice et al., "The influence of immaturity on hypoxic-ischemic brain damage in the rat," Ann Neurol, 1981, 9:131-141.
Robertson and Finer, "Term infants with hypoxic-ischemic encephalopathy: Outcome at 3.5 years," Dev Med Child Neurol, 1985, 27:473-484.
Robertson et al., "Melatonin augments hypothermic neuroprotection in a perinatal asphyxia model," Brain, 2013, 136:90-105.
Rossiter et al., "Caspase-3 activation and caspase-like proteolytic activity in human perinatal hypoxic-ischemic brain injury," Acta Neuropathol, 2002, 103:66-73.
Savaskan et al., "Reduced hippocampal mt2 melatonin receptor expression in alzheimer's disease," J Pineal Res, 2005, 38:10-16.
Schmued et al., "Fluoro-jade: A novel fluorochrome for the sensitive and reliable histochemical localization of neuronal degeneration," Brain Res, 1997, 751:37-46.
Signorini et al., "Free iron, total f-isoprostanes and total f-neuroprostanes in a model of neonatal hypoxic-ischemic encephalopathy: Neuroprotective effect of melatonin," J Pineal Res, 2009, 46:148-154.
Srinivasan et al., "Melatonin in Alzheimer's disease and other neurodegenerative disorders," Behav Brain Funct, 2006, 2:15.
Stanimirovic et al., "Stimulation of glutamate uptake and Na,K-ATPase activity in rat astrocytes exposed to ischemia-like insults," Glia, 1997, 19:123-134.
Swanson et al., "Astrocyte energetics, function, and death under conditions of incomplete ischemia: A mechanism of glial death in the penumbra," Glia, 1997, 21:142-153.
Thomas et al., "Melatonin receptors in human fetal brain: 2-[(125)i]iodomelatonin binding and mt1 gene expression," J Pineal Res, 2002, 33:218-224.
Thoresen et al., "Posthypoxic cooling of neonatal rats provides protection against brain injury," Arch Dis Childhood, Fetal Neonat Ed. 1996, 74:F3-9.
Wang et al., "Inhibitors of cytochrome c release with therapeutic potential for Huntington's disease," J Neurosci, 2008, 28:9473-9485.
Wang et al., "Methazolamide and melatonin inhibit mitochondrial cytochrome c release and are neuroprotective in experimental models of ischemic injury," Stroke, 2009, 40:1877-1885.
Wang et al., "The melatonin mtl receptor axis modulates mutant huntingtin-mediated toxicity," J Neurosci, 2011, 31:14496-14507.
Wang et al., "Role of Wnt1 and Fzd1 in the spinal cord pathogenesis of amyotrophic lateral sclerosis-transgenic mice," Biotechnology Letters, Aug. 2013, 35(8):1199-207.
Wang, "The antiapoptotic activity of melatonin in neurodegenerative diseases," CNS Neuroscience & Therapeutics, Dec. 2009, 15(4):345-57.
Wang, "The antiapoptotic effects of melatonin in neonatal hypoxic-ischemic brain injury and adult ischemic stroke," JSM Neurosurg Spine, Apr. 14, 2014, 2(4):1033.
Weil et al. "Melatonin receptor (MT1) knockout mice display depression-like behaviors and deficits in sensorimotor gating," Brain Research Bulletin, Feb. 2006, 68(6):425-9.
Weishaupt et al., "Reduced oxidative damage in als by high-dose enteral melatonin treatment," J Pineal Res, 2006, 41:313-323.

(56) References Cited

OTHER PUBLICATIONS

Welin et al., "Melatonin reduces inflammation and cell death in white matter in the mid-gestation fetal sheep following umbilical cord occlusion," Pediatric Research, Feb. 2007, 61(2):153-158.

Wong et al., "Melatonin ameliorates brain injury induced by systemic lipopolysaccharide in neonatal rats," Neuroscience, May 2014, 267:147-156.

Wu et al., "Neuroprotective agents for neonatal hypoxic-ischemic brain injury," Drug Dis Today, Nov. 2015, 20(11):1372-1381.

Wu et al., "Alterations of melatonin receptors MT1 and MT2 in the hypothalamic suprachiasmatic nucleus during depression," Journal of Affective Disorders, Jun. 1, 2013, 148(2-3):357-367.

Young, et al., "Different pathways lead to mitochondrial fragmentation during apoptotic and excitotoxic cell death in primary neurons," Journal of Biochemical and Molecular Toxicology, Sep. 2010, 24(5):335-341.

Zarei et al., "A comprehensive review of amyotrophic lateral sclerosis," Surg Neurol Int, 2015, 6: 171.

Zhang et al., "Melatonin inhibits the caspase-1/cytochrome c/caspase-3 cell death pathway, inhibits mt1 receptor loss and delays disease progression in a mouse model of amyotrophic lateral sclerosis" Neurobiol Dis, 2013, 55:26-35.

Zhang et al. "Dipyrone Inhibits Neuronal Cell Death and Diminishes Hypoxic/Ischemic Brain Injury," Neurosurgery, Oct. 2011, 69(4):942.

Zhou et al., "N-acetyl-serotonin offers neuroprotection through inhibiting mitochondrial death pathways and autophagic activation in experimental models of ischemic injury," Journal of Neuroscience, Feb. 2014, 34(8):2967-78.

Merchant et al, "Pharmacokinetics of melatonin in preterm infants," BJCP, 2013, 76:5:725-233.

\* cited by examiner

MOLECULES IN THE TRYPTOPHAN-5-HYDROXYTRYPTOPHAN-SEROTONIN-NAS-MELATONIN/6-HYDROXY-MELATONIN SULFATE-MELATONIN RECEPTOR 1A PATHWAY IN NEUROLOGICAL DISEASES

CLAIM OF PRIORITY

This application claims the benefit of U.S. Provisional Application Ser. No. 62/502,827, filed on May 8, 2017. The entire contents of the foregoing are incorporated herein by reference.

SEQUENCE LISTING

The instant application contains a Sequence Listing which has been submitted electronically in ASCII format and is hereby incorporated by reference in its entirety. Said ASCII copy, created on Oct. 28, 2019, is named SequenceListing.txt and is 1.52 MB in size.

TECHNICAL FIELD

Described herein are methods that include determining levels of melatonin pathway agents (melatonin, L-tryptophan, 5-hydroxytryptophan (5-HTP), serotonin, N-acetylserotonin (NAS), and melatonin receptor 1A (MT1)) in Hypoxic-ischemic brain injury in both newborns (HIE) and adults (stroke), and in ALS, and optionally administering these agents to treat these conditions.

BACKGROUND

Melatonin (N-acetyl-5-methoxytryptamine), a full agonist of melatonin receptor 1A (MT1), has been in clinical use for many years.

SUMMARY

As demonstrated herein, tryptophan, 5-HTP, Serotonin, NAS, Melatonin/6-HMS, and Melatonin receptor A levels are reduced in HIE and/or ALS patients, as well as in H-I brain injury mouse pups and/or mSOD1G93A ALS transgenic mice. For examples, the HIE study presented herein identified a correlation between urinary 6-HMS, serotonin, 5-HTP, and tryptophan levels and outcomes/disease severity of brain injury (mild, moderate, and severe) in human newborns with HIE. Melatonin blood levels were significantly reduced in ALS patients when compared with healthy control subjects and were significantly decreased in neonatal H-1 brain injury pups and in mSOD1G93A ALS transgenic mice. The present data demonstrates that a cascade of molecules in the tryptophan-5-hydroxytryptophan (5-HTP)-Serotonin-NAS-Melatonin/6-hydroxymelatonin sulfate (6-HMS)-Melatonin receptor 1A (MT1) pathway can be used as diagnostic/prognostic biochemical biomarkers for HIE/stroke and ALS.

Thus, provided herein are methods for treating a subject who has one or more symptoms of amyotrophic lateral sclerosis (ALS). The methods include providing a sample comprising blood or urine from the subject; determining (e.g., performing an assay to determine) a level of one or more melatonin pathway agents selected from the group consisting of melatonin, L-tryptophan, 5-hydroxytryptophan (5-HTP), serotonin, N-acetylserotonin (NAS), and melatonin receptor 1A (MT1)) in the sample; identifying a subject who has a level of the agent above a reference level; and administering a treatment for ALS to the subject.

In some embodiments, the treatment comprises administration of one or more agents selected from the group consisting of melatonin, 5-HTP, serotonin, and NAS. In some embodiments, the treatment comprises administration of melatonin or NAS.

In some embodiments, the sample comprises serum; these methods can include determining a level of one or more melatonin pathway agents selected from the group consisting of melatonin, NAS, serotonin, and MT1 in the sample.

Also provided herein are methods for diagnosing and treating a newborn subject who is suspected of having hypoxic-ischemic encephalopathy (HIE). The methods include providing a sample comprising blood or urine from the subject; determining (e.g., performing an assay to determine) a level of one or more melatonin pathway agents selected from the group consisting of melatonin, L-tryptophan, 5-hydroxytryptophan (5-HTP), serotonin, N-acetylserotonin (NAS), and melatonin receptor 1A (MT1)) in the sample; identifying a subject who has a level of the agent above a reference level; and administering a treatment for HIE to the subject.

In some embodiments, the treatment comprises administration of one or more agents selected from the group consisting of melatonin, 5-HTP, serotonin, and NAS. In some embodiments, the treatment comprises administration of melatonin or NAS. In some embodiments, the treatment comprises administration of hypothermia.

In some embodiments, the sample comprises urine; optionally, these methods can include determining a level of one or more melatonin pathway agents selected from the group consisting of tryptophan, melatonin, 5-HTP, serotonin, and MT1 in the sample.

In some embodiments, the sample comprises blood; optionally, these methods can include determining a level of one or more of melatonin, serotonin, or 5-HTP.

In some embodiments, the subject is a newborn, and the sample is obtained from the newborn subject within 2-24, or 12-24 hours of birth.

In some embodiments, the subject is an adult.

In some embodiments of the methods described herein, the subject does not have sleep disturbance.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
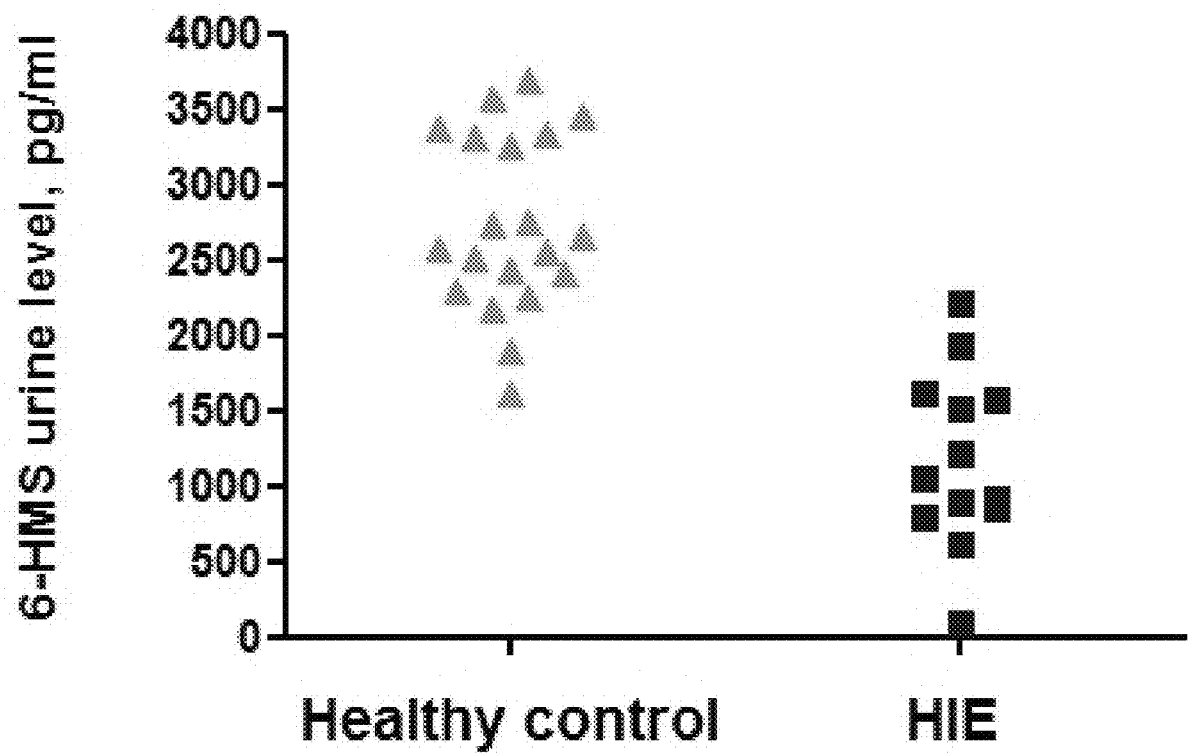
FIG. 1. 6-HMS levels were significantly lower in urine samples of HIE than in control subjects. Urine samples were collected from healthy subjects (n=20) and HIE (n=13) and tested by 6-HMS ELISA kit. Measured samples were quantified by standard curves to obtain the concentrations of targeting 6-HMS. p<0.001 (t-test).

Intensive research by us and others has indicated melatonin's benefits in both the experimental models and clinical treatments of neurological disorders including amyotrophic lateral sclerosis (ALS),[11-13] Huntington's disease,[14, 15] Alzheimer's disease,[16, 17] Parkinson's disease,[18] multiple sclerosis,[19] and adult ischemic stroke.[30, 21] However, there are only a few reports related to melatonin's role in the neonatal animal model of H-I brain injury, while to our knowledge no report in the mouse unilateral carotid ligation and hypoxia model of H-I brain injury has been published.[5, 22-27]

Melatonin has multiple functions in treating H-I brain injury, including anti-apoptotic, anti-oxidative, anti-excitotoxic, and anti-inflammatory properties, while its other protective mechanism is activation of survival signal pathways.[5, 26, 28-31]

The Melatonin Pathway—Diagnostic and Therapeutic

Melatonin is synthesized in mammals from L-tryptophan via 5-hydroxytryptophan (5-HTP), serotonin, and N-acetylserotonin (NAS). Melatonin acts on melatonin receptors and signals via multiple intracellular pathways, including inhibition of cyclic AMP and cyclic GMP, activation of protein kinase C and extracellular signal-regulated protein kinase-ERK1/2.[54] In addition to its receptor-independent actions, it is clear that melatonin influences neural physiology via membrane receptors.[34, 56] We and other researchers have also reported that the overexpression of MT1 is neuroprotective, and MT1 is less abundant in apoptotic striatal cells,[14] as well as in brain of R62 Huntington's disease transgenic mice[14], and spinal cord of mSOD1$^{G93A}$ ALS transgenic mice,[11] while MT2 remains stable in cellular systems and in ALS mice.[11, 14] Moreover, melatonin corrects the MT1 deficiency, and melatonin-mediated neuroprotection is dependent upon the presence and activation of MT1 in brain tissues of Huntington's disease mice and spinal cords of amyotrophic lateral sclerosis mice.[11, 14] However, the activation of melatonin receptors under hypoxic conditions and stroke is controversial and limited to only a few studies.[55, 57, 58, 59, 60] There is no reported study on acute H-I brain injury in newborns on the expression of MT1 receptors.

As shown herein, levels of each of these melatonin pathway agents (melatonin, L-tryptophan, 5-hydroxytryptophan (5-HTP), serotonin, N-acetylserotonin (NAS), and melatonin receptor 1A (MT1)) are altered in Hypoxic-ischemic brain injury in both newborns (HIE) and adults (stroke), and in ALS. Furthermore, administration of these agents had positive effects on parameters of disease in animal models. Thus, the present methods can be used for diagnosing and treating subjects with these conditions. Below are the structures of each of the agents.

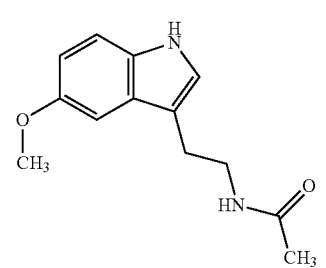

Melatonin, N-[2-(5-methoxy-1H-indol-3-yl)ethy]:

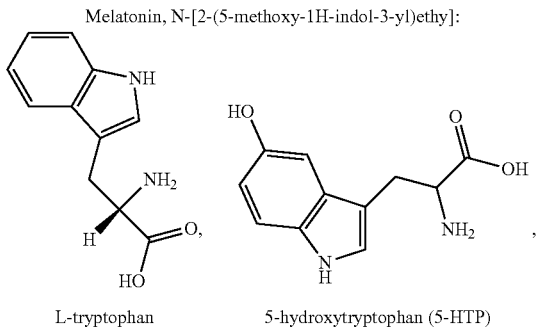

L-tryptophan         5-hydroxytryptophan (5-HTP)

-continued

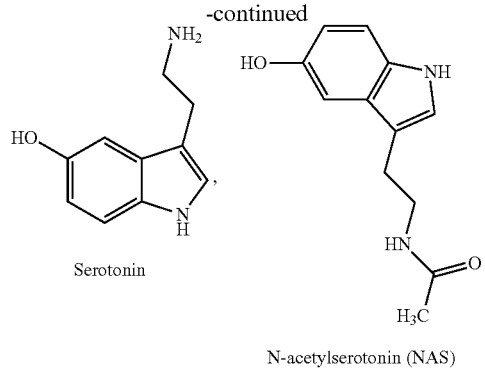

Serotonin,

N-acetylserotonin (NAS)

The melatonin receptor 1A (MT1) is also known as MTNR1A, and exemplary sequences for human MT1 are available in GenBank at Acc. No. NM_005958.4 (mRNA) NP_005949.1 (protein).

The present study provides experimental support for the use of melatonin and melatonin pathway compounds as diagnostics and therapy for newborn H-I brain injury, ALS, and stroke. Our study shows that low dose melatonin during and immediately after H-I injury protects the newborn brain. In our study doses of 10 mg/kg caused 60% reduction in brain damage compared to 64% reduction at a dose of 15 mg/kg seen by Carloni et al.[22] The hippocampus, which represents one of the most affected areas after hypoxia-ischemic, appeared particularly protected (57% reduction). Studies have shown the neuroprotective effects of melatonin both in adult and newborn models of stroke or H-I injury when administered before or after ischemia.[20, 22, 71] The use of melatonin in conditions of oxidative stress in human newborns like asphyxia, sepsis and respiratory distress syndrome has demonstrated good safety profile with no significant complications.[72, 73] When combined with hypothermia, melatonin enhances neuroprotection by reduction of the hypoxia-ischemia induced increase in clinically relevant biomarkers in the deep grey matter of newborn piglets.[25] A randomized control pilot study showed that the combination of melatonin and hypothermia in infants with moderate to severe HIE was efficacious in reducing oxidative stress and improving survival with favorable neurodevelopmental outcomes at 6 months of age.[74]

Besides the vital role of melatonin in the GPCR signaling pathway, its small molecular size, high lipophilicity, excellent blood-brain barrier permeability and minimal side effects in humans makes it an attractive option for neuroprotection.[31, 75] The alteration in the expression of MT1 and melatonin levels in newborn H-I injury provides a functional biomarker for these conditions. This can be used in disease stratification so that neuroprotective strategies may be appropriately tailored depending on severity of injury and offer hope to babies and adults with this devastating condition.

Hypoxic-Ischemic (H-I) Brain Injury

Hypoxic-ischemic (H-I) brain injury in the perinatal period is a major cause of morbidity and mortality in newborns resulting in adverse neurological outcomes including epilepsy, learning disabilities and cerebral palsy.[1] The underlying mechanisms leading to cell death in the brain after newborn H-I injury are complex and not completely understood.[2] A variety of strategies have proven to be neuroprotective against H-I brain injury in newborn animal models including those targeting the excitotoxic cascade,[3, 4] oxidative stress,[5] growth factors,[6] apoptosis,[7] and those acting on multiple pathways such as hypothermia.[8, 9] Of these potential therapies, it is disappointing that hypothermia is the only neuroprotective intervention that has translated to some clinical benefit in newborn babies with hypoxic-ischemic encephalopathy (HIE).[9] Moreover, hypothermia is only partially effective and clinical trials have shown that more than 40% of cooled infants died or survived with impairment;[10] thus, there is great interest in identifying additional potential therapeutic drugs.

In the post-neonatal period, ischemic brain injury (or stroke) can also be associated with severe impairment.

In some embodiments, the subjects treated using a method described herein are subjects who do not have sleep disturbance Amyotrophic Lateral Sclerosis (ALS)

ALS is a fatal neurodegenerative disease that typically develops later in life and is associated with degeneration of cortical and spinal motor neurons leading to progressive muscle paralysis. Most ALS cases are sporadic (not apparently running in families; often referred to as sALS), but 5-10% of the cases are familial ALS (fALS). Symptoms are described in Zarei et al., Surg Neurol Int. 2015; 6: 171. The present methods can be used to assist in diagnosing the disease (e.g., in addition to evaluation of symptoms and electrophysiological, laboratory, and neuroimaging testing; see Zarei et al., 2015), and in treating subjects who have been diagnosed.

Methods of Diagnosis

Included herein are methods for diagnosing ALS and ischemic brain injury in newborns and adults. The methods rely on detection of a biological marker or a plurality of biological makers of a particular disease state or disease susceptibility. Biological markers used in the present methods include one or more melatonin pathway agents (melatonin, L-tryptophan, 5-hydroxytryptophan (5-HTP), serotonin, N-acetylserotonin (NAS), and/or melatonin receptor 1A (MT1)). The methods include obtaining a sample from a subject, and evaluating the presence and/or level of the melatonin pathway agent(s) in the sample, and comparing the presence and/or level with one or more references, e.g., a control reference that represents a normal level of the agent(s), e.g., a level in an unaffected subject, and/or a disease reference that represents a level of the proteins associated with ALS or stroke/HIE, e.g., a level in a subject having ALS or stroke/HIE. Suitable reference values can include those shown herein.

As used herein the term "sample", when referring to the material to be tested for the presence of a biological marker using the method of the invention, includes inter alia whole blood, plasma, serum, urine, or cerebrospinal fluid. The type of sample used may vary depending upon the identity of the biological marker to be tested and the clinical situation in which the method is used. In preferred embodiments, a sample is obtained from subjects who are suspected of having HIE as early as possible, e.g., less than 12 hours after birth, up to 24 hours after birth, up to 2 days after birth, or up to 3-4 days after birth. In preferred embodiments, a sample is obtained from subjects who are suspected of having a stroke as early as possible, e.g., less than 2-12 hours after the suspected stroke, up to 24 hours after the stroke, up to 2 days after the stroke, or up to 3-4 days after the stroke.

Various methods are well known within the art for the identification and/or isolation and/or purification of a biological marker from a sample. An "isolated" or "purified" biological marker is substantially free of cellular material or other contaminants from the cell or tissue source from which the biological marker is derived i.e. partially or completely altered or removed from the natural state through human intervention. For example, nucleic acids contained in the sample are first isolated according to standard methods, for example using lytic enzymes, chemical solutions, or isolated by nucleic acid-binding resins following the manufacturer's instructions.

The presence and/or level of an agent can be evaluated using methods known in the art, e.g., using standard electrophoretic and quantitative immunoassay methods for proteins, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84(14):6008-6015; Brody (2010) Expert Rev Mol Diagn 10(8):1013-1022; Philips (2014) PLOS One 9(3): e90226; Pfaffe (2011) Clin Chem 57(5): 675-687). The methods typically include revealing labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to an antibody or probe, as well as indirect labeling of the probe or antibody (e.g. horseradish peroxidase, HRP) by reactivity with a detectable substance.

In some embodiments, an ELISA method may be used, wherein the wells of a mictrotiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically a sample is fixed with formalin or paraformaldehyde, embedded in paraffin, and cut into sections for staining and subsequent inspection by confocal microscopy. Current methods of IHC use either direct or indirect labelling. The sample may also be inspected by fluorescent microscopy when immunofluorescence (IF) is performed, as a variation to IHC.

Mass spectrometry, and particularly matrix-assisted laser desorption/ionization mass spectrometry (MALDI-MS) and surface-enhanced laser desorption/ionization mass spectrometry (SELDI-MS), is useful for the detection of biomarkers of this invention. (See U.S. Pat. Nos. 5,118,937; 5,045,694; 5,719,060; 6,225,047)

In some embodiments, the presence and/or level of an agent is comparable to the presence and/or level of the protein(s) in the disease reference, and the subject has one or more symptoms associated with the disease, then the subject has the disease (e.g., can be diagnosed with the disease). In some embodiments, the subject has no overt signs or symptoms of the disease, but the presence and/or level of one or more of the proteins evaluated is comparable to the presence and/or level of the protein(s) in the disease reference, then the subject has an increased risk of developing the disease. In some embodiments, once it has been determined that a person has the disease, or has an increased risk of developing the disease, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of the agent, e.g., a control reference level that represents a normal level of the agent, e.g., a level in an unaffected subject or a subject who is not at risk of developing a disease described herein, and/or a disease reference that represents a level of the proteins associated with conditions associated with the agent, e.g., a level in a subject having the disease.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein. In some cases it may be desirable that the control subject is a normal healthy individual.

A disease reference subject is one who has (or has an increased risk of developing) the disease. An increased risk is defined as a risk above the risk of subjects in the general population.

Thus, in some cases the level of an agent in a subject being less than or equal to a reference level of the agent is indicative of a clinical status (e.g., indicative of a disorder as described herein). In other cases the level of the agent in a subject being greater than or equal to the reference level of the agent is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of the agent in a subject being equal to the reference level of the agent, the "being equal" refers to being approximately equal (e.g., not statistically different).

The predetermined value can depend upon the particular population of subjects (e.g., human subjects) selected. For example, an apparently healthy population will have a different 'normal' range of levels of the agent than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Also provided herein are kits for use in the diagnostic methods that include reagents for detecting the melatonin pathway agents, e.g., antibodies that bind specifically to the agents, e.g., as known in the art. The kits can also include other reagents, e.g., control samples, detection agents, or diluents. The kits can include, e.g., test strips or other assay formats, preferably rapid, sensitive, specific, and portable assay/filter or small device to diagnose disease by testing the change of melatonin/6-HMS/NAS/Serotonin/5-HTP/Tryptophan/MT1 (single or pool panel of biomarkers), e.g., using Immune Colloidal Gold Technique (ICG Technique) or a Rapid "Dip-Stick" Assay.

Small portable device can be regular small size lab machine, or cell phone meter, pocket photometer, wearable wrist meter, etc.

Methods of Treatment

The methods described herein include methods for the treatment of ALS and HIE/stroke. Generally, the methods include administering a therapeutically effective amount of an agent as described herein, to a subject who is in need of, or who has been determined to be in need of, such treatment.

As used in this context, to "treat" means to ameliorate at least one symptom of the disorder. For example, administration of a therapeutically effective amount of a compound described herein to a subject who has ALS or stroke/HIE will result in a decrease in symptoms or neuronal loss, a reduction in rate of worsening symptoms or neuronal loss, an improvement in symptoms, and/or an increase in longevity. Neuronal loss can be evaluated by determining severity of symptoms (e.g., for ALS: abnormal fatigue of the arms and/or legs, slurred speech, muscle cramps and twitches, and/or uncontrollable periods of laughing or crying, tripping, dropping things, muscle weakness, tremor, spasm, paralysis, or voluntary movement, inter alia; for HIE: developmental delays, epilepsy, motor skill development delays, neurodevelopment delays, cognitive ability, speech, muscle tone, or voluntary movement, inter alia; for stroke: loss of balance, dizziness, muscle weakness, facial paralysis, numbness, difficult speech, impaired vision, cognitive ability, speech, muscle tone, or voluntary movement).

The methods described herein include the use of pharmaceutical compositions comprising a melatonin pathway agent as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

In addition to or as an alternative to the present methods, other methods can be used to treat subjects diagnosed with ALS using a method described herein, including FDA-approved riluzole or edaravone as well as others such as anti-apoptotic agents, anti-inflammatory agents, anti-excitotoxic/antiglutamaturgic agents, antioxidant agents, anti-aggregation agents, and neuroprotective/neurotrophic growth factors, among others (see Zarei et al., 2015), including palliative measures. In some embodiments, the ALS subjects treated using a method described herein are adult subjects not known to have experienced an ischemic event, and/or subjects who do not have sleep disturbance.

In addition to or as an alternative to the present methods, other methods can be used to treat subjects who are diagnosed with stroke/HIE using a method described herein, including administration of hypothermia for newborns, or Tissue Plasminogen Activator (tPA) for stroke.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the Examples below.

Human samples include baby urine, baby blood and umbilical cord blood of newborn HIE (obtained up to 12 hours, or up to 3-4 days after birth, adult ALS blood and CSF samples as well as healthy control subjects and/or mimic ALS. Clinical outcomes include Apgar score/cord pH/MRI findings/days of hospitalization for newborn HIE and ALS-FRS, vital capacity, disease duration, day of visit, etc. for ALS.

Animal samples in vivo include blood, brain/hippocampus/cortex, spinal cord, muscle from Middle Cerebral Artery Occlusion (MCAO) mouse model of ischemic stroke, hypoxia-ischemic mouse model of neonatal brain injury, alcohol-induced rat model of brain injury, and mSOD1G93A ALS transgenic mouse model of ALS as well as matched control animals. We also have data from MT1 knockout mice.

Animal samples ex vivo include organotypic hippocampal slice cultures of stroke.

Cell culture samples in vitro include primary hippocampal neurons and primary cortical neurons.

ELISA Assay.

Human and animal samples were measured by human or mouse melatonin/6-HMS/MT1/Serotonin/5-HTP/Tryptophan ELISA kit. Samples were quantified by standard curves to obtain the concentrations of targeting biomarker candidates. T-test was used for statistical analysis. Human samples include baby urine, baby blood and umbilical cord blood of newborn HIE, adult ALS blood and CSF samples as well as healthy control subjects and/or mimic ALS. Animal samples include blood from MCAO mouse, hypoxia-ischemic pups of mice, alcohol-induced rats, and mSOD1G93A ALS mouse and control animals.

Liquid Chromatography-Mass Spectrometry (LC/MS).

Blood samples and brain tissues form human and/or mice were obtained, cold methanol was added to aliquots of homogenate followed by centrifugation at 14,000 rpm for 15 min to collect the supernatant, which was tested by LC/MS. Measured samples were quantified by standard curve to obtain the concentration of targeting NAS.

Western Blot Analysis.

Protein samples from the lumbar spinal cord of ALS patients and control samples or brains of MCAO mice and control mice were obtained. Protein samples were analyzed for the expression of MT1 proteins using MT1 antibody with ☐-actin as the internal control.

RT-PCR Assay.

Human samples were obtained from the lumbar spinal cord of ALS patients and control samples from non-neurologic patients. Spinal cord samples were analyzed for the expression of MT1 mRNAs with GAPDH as the internal control. The human-specific MT1 primers were used for RT-PCR assay. Statistical significance was evaluated by t-test.

Immunostaining.

MT1 immunostaining with MT1 antibodies and DAPI staining in the lumbar regions of spinal cords were performed in sections of spinal cord from non-neurologic patients and ALS patients. ALS mice in late-stage and WT littermates were sacrificed. Gastrocnemius in the hindlimb of mice were dissected, postfixed and the frozen sections (18 µm) were immunstained with MT1 antibodies.

Hematoxylin and Eosin (H&E) Staining, Fluoro-Jade B (FJB) Staining, and Nissl Staining.

H&E staining and FJB staining were performed on the neonatal mice brain post-H-I injury comprising of right unilateral carotid ligation and then hypoxia. Brain sections of either 50 µm thickness with H&E or 16 µm thickness with FJB were stained and examined under microscope. Nissl staining was performed in mSOD1G93A ALS mice and wild type littermates. Serial lumbar spinal cords were sectioned at 18 µm. Continuous 10 sections per mouse were subjected to Nissl staining. Stained motor neurons were counted in the ventral horns of all sections.

Evaluation of Motor Function, Onset, and Survival, and Body Weight.

Motor strength and coordination were evaluated using a rotarod. Mice were evaluated at both 15 and 5 rpm rotarod speeds. Disease onset was defined as the first day that the mouse failed to complete 7 min at 15 rpm. Mortality was defined as the age at death or when the mouse was unable to right itself within 30 second. Body weight was monitored weekly.

Determination of Neurological Score and Infarct Volume.

MCAO was sustained for 24 h, after which each mouse was assigned a neurological score, and brains were removed for 2,3,5-triphenyltetrazolium chloride (TTC) staining, and infarct volume was measured.

Examples for Neonatal H-I Brain Injury

Animals and Surgical Procedure

All surgical and experimental procedures were carried out in accordance with the Guide for the Care and Use of Laboratory Animals approved by the Institutional Animal Care and Use Committee of Harvard Medical School. A model of hypoxia-ischemia in newborn mice pups based on modification of Rice-Vannucci model of unilateral carotid ligation (UCL) followed by hypoxia was used.[40] C57/BL6 wild type and MT1 knockout (KO) mice litters of postnatal day 8 (P8) pups were anesthetized with 2.5% isofluorane and balanced room air, and the right common carotid artery permanently ligated. Time to anesthesia and completion of surgery was timed with a stopwatch to limit the procedure to less than 3 min. Following recovery from anesthesia after 15 min, the pups were placed in hypoxia chamber through which 8% oxygen was delivered at 6 liters per min for 60 min for histology, western blot and immunostaining and 45 mins for FJB staining. Normothermia was maintained by placing the pups in an incubator at 34° C. throughout the experiment except during hypoxia when the temperature was increased to 36° C. to counteract the cooling effect of the 8% O2 gas flow. We also tested the effect of hypoxia alone by subjecting P8 pups to 60 min hypoxia without being preceded by right UCL. Pups were then returned to their dam and housed under a 12-hour-light and 12-hour-dark cycle with food and water freely available for the interval remaining until they were sacrificed at various time points to a maximum of 1 week from injury.

Clinical Evaluation

The clinical outcomes including Apgar score/cord pH/MRI findings/days of hospitalization, etc. were collected and the severity of H-I encephalopathy baby was quantified based on overall information, e.g., for severe HIE babies: MRI findings: severed damage; Apgar score: really low: e.g., 0 in 1 min, 0 in 5 min, 0 in 10 min; Cord pH/baby pH: not normal, e.g., cord pH 6.8, bay pH 7.0. For mild HIE babies: MRI findings: normal or abnormal; Apgar score: higher e.g., 1 in 1 min, 5 in 5 min, 8 in 10 min; Cord pH/baby pH: e.g., cord pH 7.2, bay pH 7.3.

In the animal models, we defined H-I disease severity by the time of hypoxia insult, e.g., mild (45 min hypoxia), moderate (60 min hypoxia), severe (75 min hypoxia) brain injury.

Drug Administration and Tissue Preparation

Melatonin and luzindole were purchased from Sigma (St. Louis, Mo., USA). Melatonin or vehicle was administered before and after the hypoxic-ischemic insult. Mice pups received intraperitoneal (IP) injection of melatonin or vehicle in the right lower quadrant. For all experiments, each group contained equal (or nearly equal) numbers of male and female pups. Animals were allocated to receive melatonin or vehicle (0.9% saline containing 3% Tween) 30 min before ligation or this dose was followed with a repeat daily dose until sacrifice. Animals received intraperitoneal (IP) injection of a 25 μl solution containing either vehicle (3% Tween) or melatonin dissolved in vehicle. Melatonin dose of 10 mg/kg once daily was used for histology, western blot and immonstaining while dose of 5 mg/kg once daily was used for FJB staining. Pups received melatonin or vehicle 30 min before surgical procedure and this dose was followed 24 hr later by once daily dose until sacrifice. The last dose of the melatonin at various time points of 24, 48 and 168 hr was 24 hr prior to sacrifice.

For histological analyses, after various time points after H-I brain injury, mice were anesthetized with IP injection of 100 mg/kg pentobarbital and then perfused through the left ventricle with PBS. Brains were removed and immersion-fixed in 4% paraformaldehyde in 0.1 M PBS overnight at 4° C. and were subsequently cryoprotected in 30% (w/v) sucrose in 0.1 M PBS. The brains were frozen by flash freezing using 1,1,1,2-Tetrafluoroethane, and serial (50 or 16 μm) coronal sections were cut from genu of corpus callosum to the end of dorsal hippocampus using a cryostat (Leica CM1850). The sections corresponding to image 205 up to caudal hippocampus region of Allen mouse brain atlas were directly mounted on SuperFrost Plus® microscope slides.

Genotyping

Tail biopsy was performed for genotyping of MT1 KO mice (The Jackson Laboratory) by cutting less than 0.5 cm length of tail. DNA samples were extracted from tails and submitted for PCR reaction. The following primers were used: mutant: 5'-CCA GCT CAT TCC TCC ACT CAT-3' (SEQ ID NO:1) and 5'-GAA GTT TTC TCA GTG TCC CGC-3' (SEQ ID NO:2). Wild type: 5'-GAG TCC AAG TTG CTG GGC AG-3' (SEQ ID NO:3) and 5'-GAA GTT TTC TCA GTG TCC CGC-3' (SEQ ID NO:4). The bands of MT1 KO (243 bp) were obtained.

Histological Studies

Histological studies were performed to delineate the regions of the brain most affected by H-I injury and quantify the damage.

Hematoxylin and Eosin (H&E) Staining and Brain Area Loss

H&E staining was performed on the brain at 7 days post H-I injury comprising of right unilateral carotid ligation and 60 min hypoxia. Brain sections of 50 μm thickness were stained with hematoxylin and eosin (all reagents from Fisher Scientific, Santa Clara, Calif.), dehydrated in graded ethanol solutions, cleared with xylene, examined under light microscope, and subsequently scanned with Epsom V500 photo scanner for measurements.

The cross-sectional unaffected and affected areas of the hippocampus, and cortex were measured with NIH imageJ software. A total of 5 coronal slices through the same hippocampus regions were inspected for tissue loss for each animal. The total cross-sectional area in each brain region was calculated in all sections assessed, and the percentage of area loss in the lesioned hemisphere versus the unlesioned hemisphere was determined for each animal. The person performing the measurements was blinded to the study groups. Images of H & E stained sections were quantified using ImageJ software package to measure hemispheric area contralateral and ipsilateral to the H-I brain injury in order to calculate the amount of tissue lost on the ipsilateral hemisphere. The loss of brain tissue ipsilateral to the H-I injury was calculated as a percentage of the non-injured contralateral hemisphere.

Fluoro-Jade B (FJB) Staining and Histological Score

FJB staining was performed at 48 hr post H-I injury of UCL followed by 45 min hypoxia. Fluoro-Jade is an anionic fluorochrome capable of selectively staining degenerating neurons in brain slices. Coronal sections of 16 μm thickness were stained with FJB using the method adapted from Schmued and colleagues.[41] Briefly, tissues mounted on glass slides were sequentially placed in 100% ethanol for 3 min, 70% ethanol for 1 min and deionized water for 1 min. Sections were oxidized for 15 min using 0.06% $KMnO_4$ solution followed by 3 brief rinses in PBS. Slides were then immersed in a 0.001% solution of Fluoro-Jade (Histochem, Jefferson, A R) in 0.1% acetic acid for 30 min, rinsed with PBS, dried for 20 min at 45° C., cleared with xylene and cover slips applied using DPX medium.

FJB stained sections were examined under a microscope independently by 2 investigators blinded to the treatment group. A score of 0, 0.25, 0.5, 0.75, and 1 were assigned respectively for 0%, 25%, 50%, 75% or 100% area involvement with FJB-positive cells of each of the areas of the cortex and hippocampus including CA1, CA2, CA3 and dentate gyrus. The total scores for the hippocampus and cortex were compared in melatonin treated and vehicle group.

Primary Cerebrocortical Neurons, Primary Hippocampal Neurons, Primary Astrocytes and Induction of Cell Death Primary cerebrocortical neurons (PCNs) and primary hippocampal neurons (PHNs) were isolated from E14 to E16C57/BL6 mice as previously described.[14, 20] Culture of PCNs and PHNs were dissociated by treatment with trypsin and cultured in poly-D-lysine-coated dishes in neurobasal medium supplemented with 2% B27, 2 mM glutamine, 100 U/mL penicillin, and streptomycin. Experiments on PCNs or PHNs were performed after 7 days in culture.

Primary astrocytes were cultured as previously described with modification.[42] Briefly, astrocytes were isolated from cortex of 1~3 day-old pups of C57 Swiss mice by mincing the cortex tissues in HBSS. The tissue was triturated after trypsinization (0.25% trypsin with 0.02% EDTA, 10 min, 37° C.). The digestion was terminated using culture medium for astrocytes (DMEM/F12 supplemented with 10% FBS (Gibco Inc., Carlsbad, Calif., USA), 100 mg/ml streptomycin and 100 U/ml penicillin). The cell suspension was filtered with 70 μm Nylon membrane, and the filtrate was collected. After centrifugation at 2000 rpm for 5 min, the precipitate was resuspended with complete astrocyte medium, and then cells were plated on T75 culture flask pretreated with poly-D-lysine. Cultures were maintained in a humidified atmosphere of 5% $CO_2$/95% air at 37° C. and the medium was renewed every 3-5 days. When the cells grew to 80-90% confluence (about 10-14 days), the cells in flasks was shaken at 260 r/min speed at 37° C. to remove the primary microglia. The remaining cells were predominantly astrocytes. GFAP immunostaining was used to determine the purity of astrocytes and a fluorescent stain DAPI (Molecular Probes) was used to stain nuclei.

PCNs, PHNs, or primary astrocytes were preincubated with 10 μM melatonin for 2 hr before challenging them with OGD and $H_2O_2$. OGD and $H_2O_2$ was conducted as previously described.[20] Briefly, OGD was induced by culturing the cells for 3 hr of duration in glucose-free Earle's balanced salt solution and cell cultures were incubated in an anaerobic chamber. Control cultures were incubated in Earle's balanced salt solution supplemented with glucose in a normoxic atmosphere for the same period. OGD was terminated after 3 hr of duration by transferring the cells to normal culture conditions. $H_2O_2$ treatment and then the cells are kept in the normal culture conditions for 18 hr. $H_2O_2$ treatment group was induced by adding 1000 μm/L $H_2O_2$ for 18 hr. Cell death was quantitatively determined for PCNs or PHNs by lactate dehydrogenase (LDH) assay (described according to the manufacturer's instructions, Roche).[14, 20] and for primary astrocytes by MTS ([3-(4,5-dimethylthiazol-2-yl)-5-(3-carboxymethoxyphenyl)-2-(4-sulfophenyl)-2H-tetrazolium] assay[14, 43].

Terminal dUTP Nick-End Labeling Assay

The assay was performed using the DeadEnd Fluorometric terminal dUTP nick-end labeling (TUNEL) system (Promega) as specified by the manufacturer. Briefly, PCNs was untreated or induced by 1 mM $H_2O_2$, or 1 mM $H_2O_2$ and 10 μM melatonin or 1 mM $H_2O_2$, 10 μM melatonin, and 100 μM luzindole for 18 hr. PCNs were then fixed with 4% formaldehyde, permeabilized by 0.2% Triton-X-100, and incubated with the TUNEL reaction mixture for 1 hour at 37° C. After thorough washes, chromatin condensation and nuclear fragmentation were analyzed using a fluorescence microscope.[20]

Determination of Mitochondrial Transmembrane Potential

For mitochondrial transmembrane potential ($\Delta\Psi_m$), PCNs and PHNs were treated as indicated with or without 10 μM melatonin. Living cells were stained with 2 μM Rh 123 as previously described for 5 min at room temperature.[20] In digital images, reduced green Rh 123 fluorescence indicated dissipated $\Delta\Psi_m$.

Image-iTLIVE Mitochondrial Transition Pore (mPTP) Assay mPTP assays were performed according to the manufacturer's instructions (Life Technologies). Briefly, PCNs were co-incubated with 10 μM melatonin or 10 μM Cyclosporin A (CsA), an inhibitor of mPTP and a positive control, washed with modified HBSS buffer, and loaded with calcein AM and $CoCl_2$ for 15 min; 1 μM ionomycin was then added to test whether mPTP was activated. Digital images were taken.

Western Blotting

PCNs were exposed to OGD or $H_2O_2$ with or without melatonin or melatonin and luzindole. Cells were collected in ice-cold lysis buffer (20 mM Tris, pH 8.0, 137 mM NaCl, 10% glycerol, 1% Nonidet P-40, and 2 mM EDTA with 5 mM $Na_2VO_4$, protease inhibitor mixture (Roche Molecular Biochemicals) supplemented with 0.2 mM PMSF). The lysate was cleared by centrifugation at 19,720×g for 10 min at 4° C., and the supernatant was analyzed by Western blotting.[20] Following right unilateral carotid ligation (UCL), C57/BL6 P8 pups were subjected to 60 min of hypoxia. In one experiment P8 pups were subjected to 60 min hypoxia alone without being preceded by right UCL. After 12, 24, or 48 hr post H-I injury, mouse brains were homogenized on ice in RIPA buffer (1% NP-40, 0.5% sodium deoxycholate, 0.1% SDS, 142.5 mM KCl, 5 mM $MgCl_2$, 10 mM Hepes, pH 7.4) with protease inhibitor cocktail and PMSF. Lysates were centrifuged twice at 10,000×g for 20 min at 4° C. The resulting supernatants were analyzed by Western blotting.[20, 44] Protein concentration was measured by the Bradford method. Antibody to melatonin receptor 1A was purchased from Millipore Bioscience Research Reagents, caspase-3 and GFAP antibodies from Cell Signaling Technology, cytochrome c was purchased from BD Biosciences, and β-actin antibody from Sigma. Secondary antibodies and ECL reagents were from GE Healthcare.

Immunohistochemistry

Brain sections (16 μm-thick coronal cryosections) of pups were fixed by 4% paraformaldehyde for 20 min and incubated with blocking solution (normal goat serum 1:20 [v/v] in PBS) at room temperature for 1 hour, and then stained with diluted primary antibodies in 2% goat serum in PBS at 4° C. overnight (GFAP, 1:200, Rabbit, DAKO, Denmark; anti-Iba1, 1:200, Rabbit, Wako Pure Chemical Industries, Ltd. Japan; cleaved caspase-3, 1:200 Cell Signaling). Sections were incubated in diluted fluorescein labeled secondary antibody: goat anti-rabbit IgG conjugated to FITC (1:200, Vector laboratories Inc. Burlingame, Canada) at room temperature for 1 hour. Images were taken under fluorescence microscopy.

Immunocytochemistry and Measurement

PCNs exposed to OGD or $H_2O_2$ with or without 5 μM melatonin or 5 μM melatonin and 25 μM luzindole were fixed in 4% paraformaldehyde and then incubated at room temperature for a half hour with blocking solution (normal goat serum 1:20 [v/v]). Subsequently, cells were incubated with anti-Tom 20 (1:200), or GFAP (1:500), or caspase-3 (1:500) overnight at 4° C. and then incubated with FITC conjugated secondary antibody at room temperature for 1 hour. A fluorescent stain DAPI was used to visualize nuclei. Images were taken under fluorescence microscopy.

Mitochondrial length in Tom 20 experiment was measured by Image J (v. 1.43) software and Nano Measurers (v.1.2.5) software.[43] Briefly, the scale was set and scale bar was made according to the picture pixel and size. Mitochondrial length was measured by using Nano Measurers software. To compare different length of mitochondria in the cells, mitochondria were classified into different categories with a length ranging from less than 1, 1-2, 2-3, 3-4, and greater than 5 μm. A minimum of 200 mitochondria for each picture were scored. Percentage of different length mitochondria in each picture was recorded.

Data Analysis

Densitometric quantification was performed with the Quantity One Program (Bio-Rad). All quantified data were presented as mean±the standard error of the mean (SEM). Statistical significance was evaluated by One-Way ANOVA and repeated measures t-tests. Statistical significance values of * $p<0.05$ and ** $p<0.01$ were used.

Example 1. Melatonin Levels in Newborns Correlate with Presence and Severity of Hypoxic Injury Urine samples were collected from healthy subjects (n=20) and HIE patients (mild n=13) and tested by ELISA kit. Samples were quantified by standard curves to obtain the concentrations of targeting 6-HMS. As shown in FIG. 1, 6-HMS levels were significantly lowered in newborns with HIE.

Figure 2:
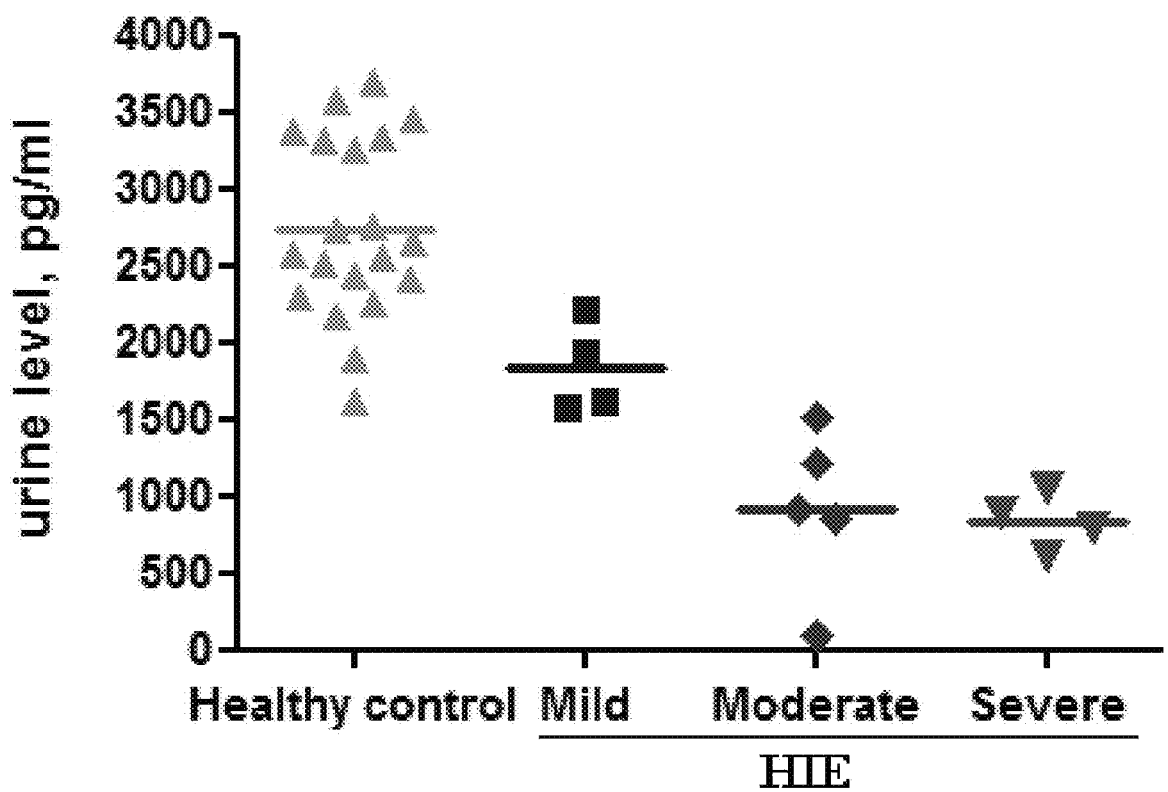
FIG. 2. 6-HMS levels were correlated with the severity of brain injury in newborns with HIE. Urine samples were collected from healthy subjects (n=20) and HIE patients (mild n=4, moderate n=5, severe n=4) and tested by ELISA kit. Samples were quantified by standard curves to obtain the concentrations of targeting 6-HMS.

In addition, urine samples were collected from healthy subjects (n=20) and HIE patients (mild n=4, moderate n=5, severe n=4) and tested by ELISA kit. Samples were quantified by standard curves to obtain the concentrations of targeting 6-HMS. As shown in FIG. 2, 6-HMS levels were correlated with the severity of brain injury in newborns with HIE.

Figure 3:
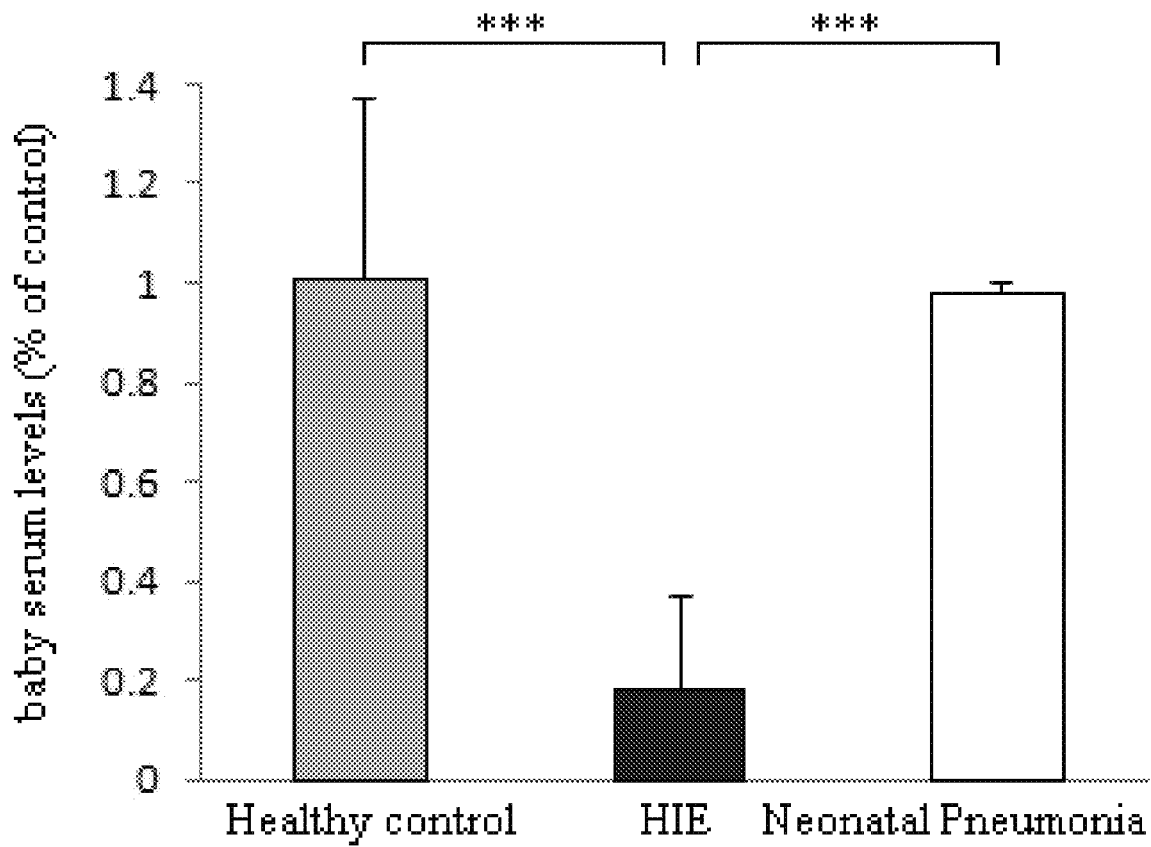
FIG. 3. Melatonin levels were reduced in baby blood samples of HIE compared with control subjects. Baby blood samples were collected in China from healthy subjects (n=4), HIE (n=3, mild), and neonatal pneumonia (n=3). The samples were centrifuged and serum were obtained and tested by ELISA kit. Measured samples were quantified by standard curves to obtain the concentration of targeting melatonin. ***p<0.001 (t-test).

In addition, baby blood samples were collected in China from healthy subjects (n=4), HIE (n=3, mild), and neonatal pneumonia (n=3). The samples were centrifuged and serum were obtained and tested by ELISA kit. Measured samples were quantified by standard curves to obtain the concentration of targeting melatonin. As shown in FIG. 3, melatonin levels were reduced in baby blood samples of HIE compared with control subjects.

Table 1 shows a comparison of melatonin cord blood levels with Apgar score, cord pH/baby pH, EEG and MRI, and days of hospitalization in HIE patients and healthy subjects. Comparison of melatonin cord blood levels with clinical short-term outcomes including Apgar score, cord pH/baby pH, EEG and MRI findings, and days of hospitalization, as well as gestational age, body weight, mode of delivery, gender, and inborn/outborn are shown in two examples of healthy subjects and two examples of HIE patients. All of the infants were Inborn (e.g., born in a hospital or other birth facility and not at home). No EEG or MRI was obtained for the Healthy subjects, while EEG and MRI were abnormal in both HIE subjects.

4, demonstrated that blood levels of melatonin in MCAO mice were greatly reduced as compared to controls.

Example 3. Melatonin Levels in Amyotrophic Lateral Sclerosis (ALS)

Figure 6A:
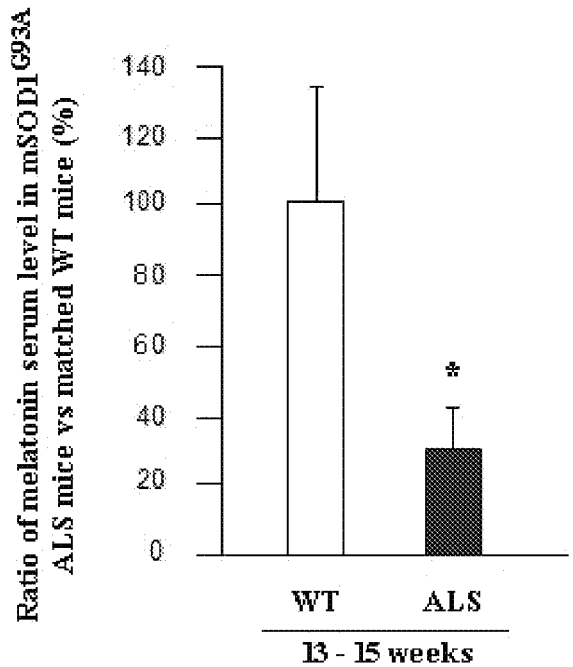
FIGS. 6A-6B. ELISA analysis of blood levels of melatonin in ALS mice. Blood samples from mSOD1G93A ALS transgenic mice and WT littermates at 13-15 weeks of age (A) and 17-19 weeks of age (B) were collected at 8-9 am. Serum samples (100 ml) were obtained and submitted for ELISA measurement (n=4-6 in A and n=10-12 in B). Both the ALS and WT mice groups were comprised of equal (or nearly equal) numbers of males and females. Data were presented as mean+SEM. * p<0.05. Statistical significance was evaluated by t test.
Figure 6B:
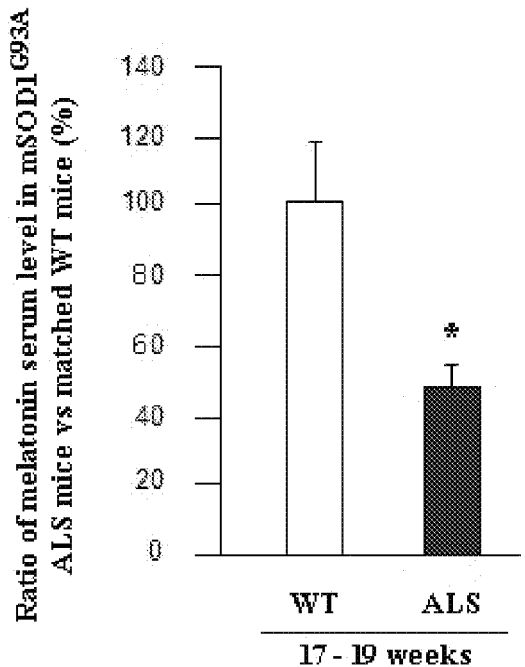

Blood samples from mSOD1G93A ALS transgenic mice and WT littermates at 13-15 weeks of age and 17-19 weeks of age were collected at 8-9 am. Serum samples (100 ml) were obtained and submitted for ELISA measurement. Both the ALS and WT mice groups were comprised of equal (or nearly equal) numbers of males and females. As shown in FIGS. 6A-6B, blood levels of melatonin in the ALS mice were greatly reduced as compared to control.

Figure 7:
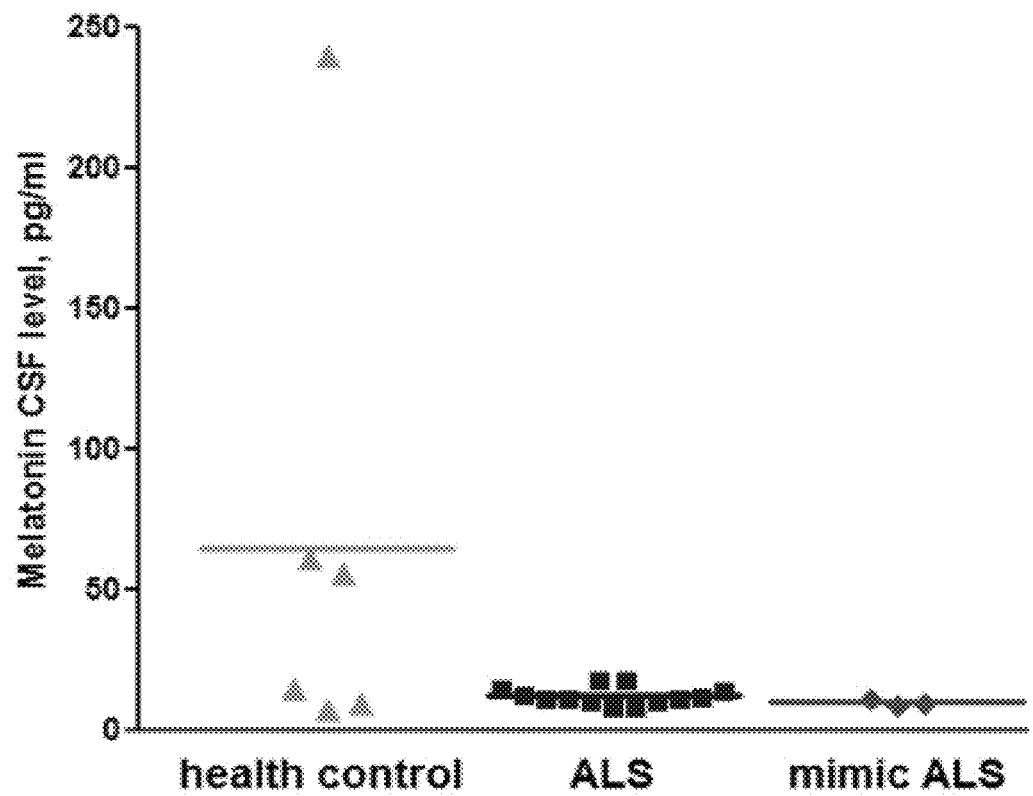
FIG. 7. Melatonin was reduced in the CSF samples of early stage of sALS patients. CSF samples were collected from early stage of sALS patients (n=13, squares), healthy control subjects (n=6, triangles), and mimic ALS patients (n=3, diamonds) at 8-10 am. Scatter plot graphs of melatonin presented the concentrations of melatonin in human samples. The average 64.5 pg/ml in the healthy control group, 12.0 pg/ml in the ALS group, and 9.8 pg/ml in the mimic ALS group. To the best of our knowledge, this is the first finding that melatonin CSF levels were reduced (5.5 fold) in ALS patients. The sensitivity (67%) and specificity (85%) of melatonin assay were calculated.

In addition, CSF samples were collected from early stage sALS patients (n=13), healthy control subjects (n=6), and mimic ALS patients (e.g., subjects with other motor neuron diseases that may mimic ALS, e.g., spinal muscular atrophy and spinobulbar muscular atrophy) (n=3) at 8-10 am. As shown in FIG. 7, melatonin was reduced in the CSF samples of early stage of sALS patients. The averages were 64.5 pg/ml in the healthy control group, 12.0 pg/ml in the ALS group, and 9.8 pg/ml in the mimic ALS group. To the best of our knowledge, this is the first finding that melatonin CSF levels are reduced (by about 5.5 fold) in ALS patients.

Figure 8:
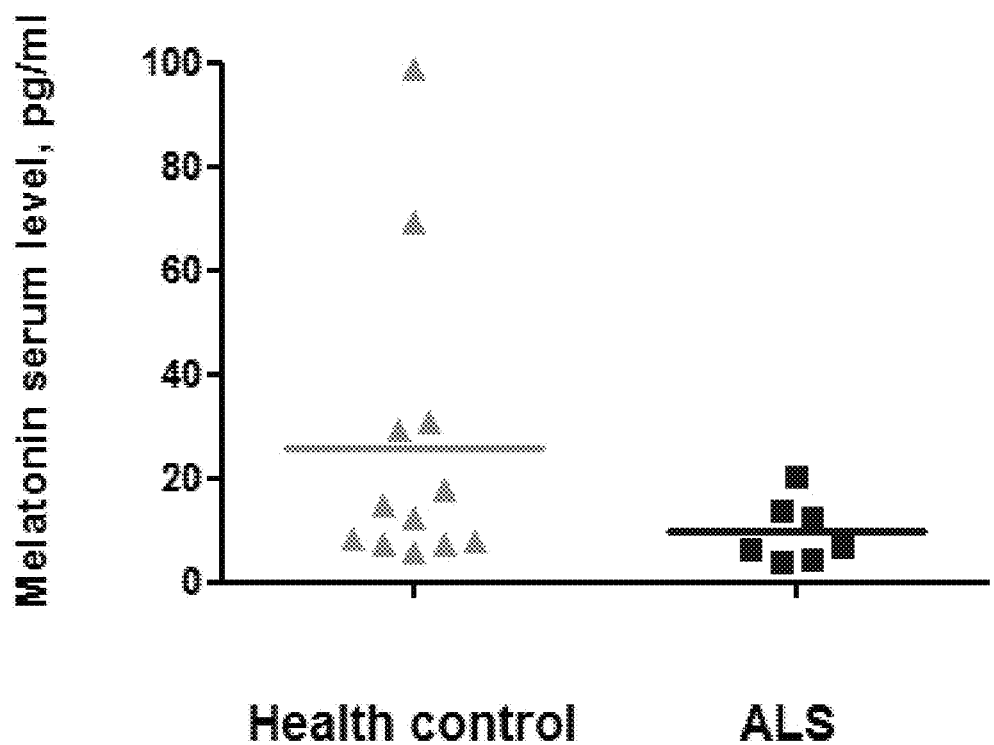
FIG. 8. Serum levels of melatonin were significantly lowered in ALS patients. Blood samples were collected from ALS patients (n=7) and a healthy control group (n=12) at 8-10 am. Serum samples (200 ml) were obtained and submitted for ELISA measurement. * p<0.05. The average 26 pg/ml in the healthy control group and 10 pg/ml in the ALS group. To the best of our knowledge, this is the first finding that melatonin blood levels were reduced (2.6 fold) in ALS patients.

Blood samples were also collected from ALS patients (n=7) and a healthy control group (n=12) at 8-10 am. Serum samples (200 ml) were obtained and submitted for ELISA measurement. As shown in FIG. 8, serum levels of melatonin were significantly lowered in ALS patients. The averages were 26 pg/ml in the healthy control group and 10

TABLE 1

Comparison of melatonin cord blood levels with clinical outcomes in newborn HIE patients

| Study ID | Melatonin (pg/ml) | Apgar score 1, 5, 10 min | Cord pH | Baby pH | Days hospitalization | GA (week) | BW (g) | Mode of delivery | Gender |
|---|---|---|---|---|---|---|---|---|---|
| Healthy No. 1 | 35.7 | 8, 9, 9 | — | — | 2 | 38.7 | 3118 | VD | Female |
| Healthy No. 2 | 24.0 | 8, 9, 9 | — | — | 4 | 39.0 | 3200 | CS | Male |
| HIE No. 1 | 10.6 | 2, 2, 4 | — | 7.30 | 4 | 37.3 | 2679 | CS | Male |
| HIE No. 2 | 15.7 | 2, 5, 7 | 6.95 | 7.17 | 12 | 39.0 | 3320 | CS | Male |

Gestational age (GA); body weight (BW); mode of delivery, VD = Vaginal Delivery.
CS = Cesarean Section.

Figure 4:
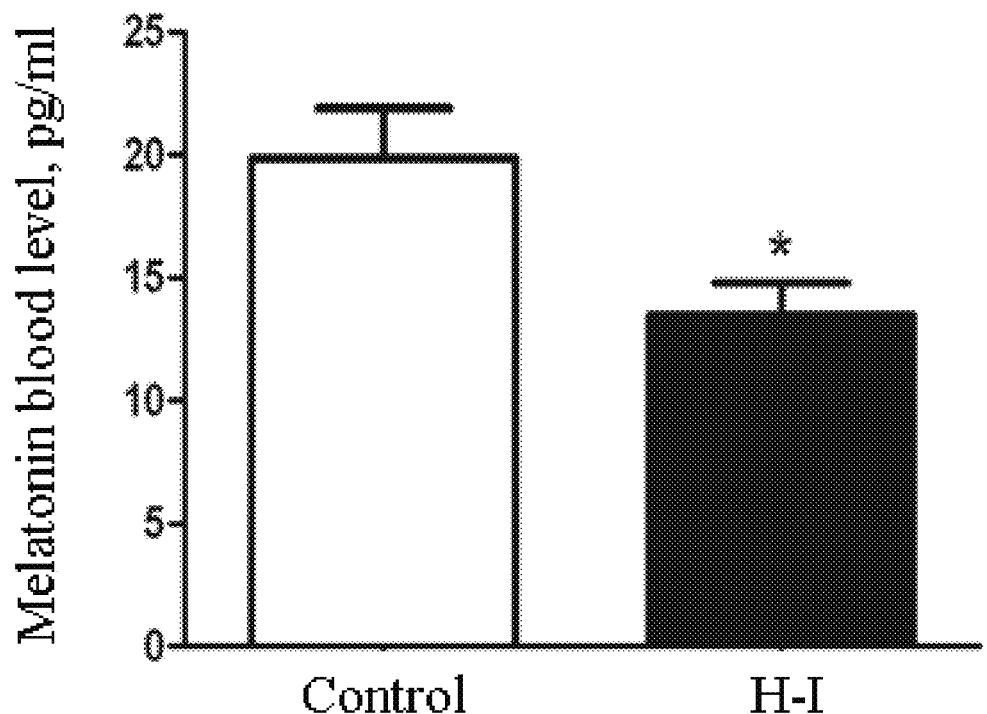
FIG. 4. Melatonin serum levels were significantly reduced in H-I pups of mice. Blood samples were collected from control pups and pups under H-I treatment (P8, n=4-6) and tested by melatonin ELISA kit. Measured samples were quantified by standard curves to obtain the concentrations of targeting melatonin. Data were presented as mean±SEM. p<0.05 (t-test). H-I: Hypoxia-ischemia.
Figure 5:
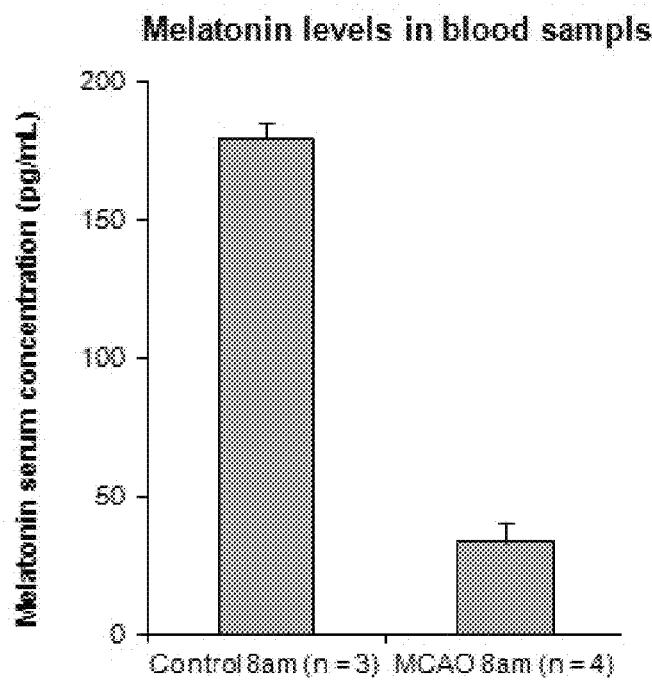
FIG. 5. ELISA analysis of blood levels of melatonin in MCAO mice. Blood samples from MCAO mice and vehicle control mice (25-30 g) were collected at 8-9 am. Serum samples (100 ml) were obtained and submitted for ELISA measurement (n=4 in MCAO group and n=3 in vehicle saline group). Both groups were comprised of equal (or nearly equal) numbers of males and females. Data were presented as mean+SEM. ** p<0.01. Statistical significance was evaluated by t test.

Similar results were seen in an animal model of newborn HIE. Blood samples were collected from control pups and pups under H-I treatment (P8, n=4-6) and tested by melatonin ELISA kit. Measured samples were quantified by standard curves to obtain the concentrations of targeting melatonin. As shown in FIG. 4, melatonin serum levels were significantly reduced in H-I pups of mice.

Example 2. Melatonin Levels in an Animal Model of Stroke

Blood samples from MCAO mice and vehicle control mice (25-30 g) were collected at 8-9 am. Serum samples (100 ml) were obtained and submitted for ELISA measurement (n=4 in MCAO group and n=3 in vehicle saline group). Both groups were comprised of equal (or nearly equal) numbers of males and females. The results, shown in FIG.

pg/ml in the ALS group. To the best of our knowledge, this is the first finding that melatonin blood levels are reduced (about 2.6 fold) in ALS patients.

Table 2 shows a comparison of NAS and melatonin serum levels with clinical information in two healthy subjects and two sporadic ALS patients. The ALS Functional Rating Scale-Revised (ALSFRS-R) is a validated questionnaire that measures physical function in performing activities of daily living. Vital capacity is the single most critical pulmonary measurement. Disease duration was calculated from date of onset of weakness to date of blood draw (days). Day of visit was relative to other visits. The earliest visit was defined as day 0; all other visits happened within a fixed three months of the first visit. Diagnostic delay represents the time (day) between symptom onset and diagnosis.

TABLE 2

Comparison of melatonin and NAS blood levels with ALSFRS and vital capacity in ALS patients

| NAS Count | Melatonin (pg/ml) | ALS FRS | Vital capacity | Disease duration (days) | Diagnostic delay (days) | Gender | Age (years) | Time (blood draw) | Day of visit | Samples Group Number |
|---|---|---|---|---|---|---|---|---|---|---|
| 150 | 99.1 | 48 | 100 | — | — | Female | 46 | 9:00 am | 10 | Healthy No 1 |
| 161 | 69.3 | 48 | 100 | — | — | Female | 69 | 9:30 am | 52 | Healthy No 2 |
| 26 | 6.3 | 39 | 57 | 620 | 309 | Male | 47 | 9:00 am | 10 | sALS No 1 |
| 17 | 12.2 | 28 | 65 | N/A | N/A | Male | 58 | 9:00 am | 62 | sALS No 2 |

Figure 9A:
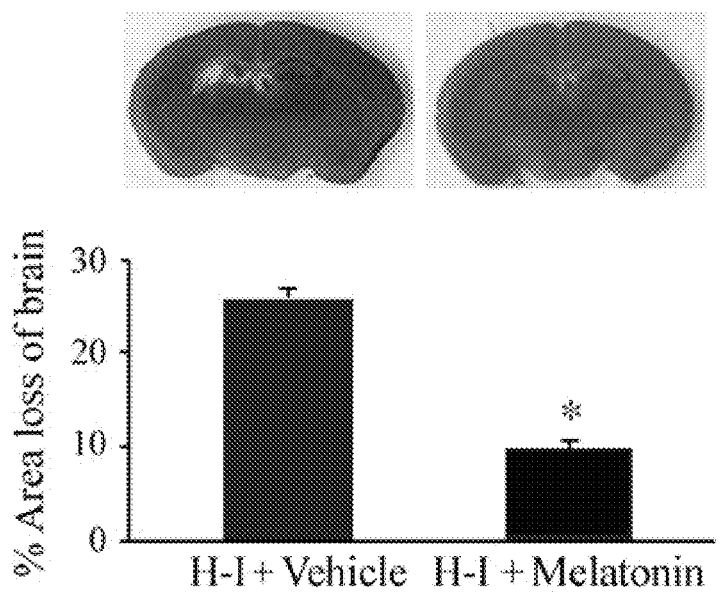
FIGS. 9A-9D. Reduction in hippocampal and cortical damage with melatonin treatment. P8 mice underwent unilateral carotid ligation followed by 60 min (A, B) or 45 min of hypoxia (C, D). Melatonin 10 mg/kg (A, B) or 5 mg/kg (C, D), or 3% Tween was performed 30 min before hypoxia-ischemia and then administered once daily until sacrifice at 7 d (A, B) or 2 d (C, D). Coronal sections of brains were obtained and stained with H&E (A, B) or Fluoro-Jade B (C, D). The percentage area loss in whole brain hemisphere and hippocampus was determined. Representative images were shown for the whole brain (A) and hippocampus (B). The vulnerability of specific areas in the brain by hypoxia-ischemia was studied by Fluoro-Jade B staining, and the histological score was calculated. Representative photomicrographs were shown (C, D). <0.05, **P<0.01. Data were presented as the mean plus or minus the standard error of the mean for each group. Scale bars correspond to 1000 μm.
Figure 9B:
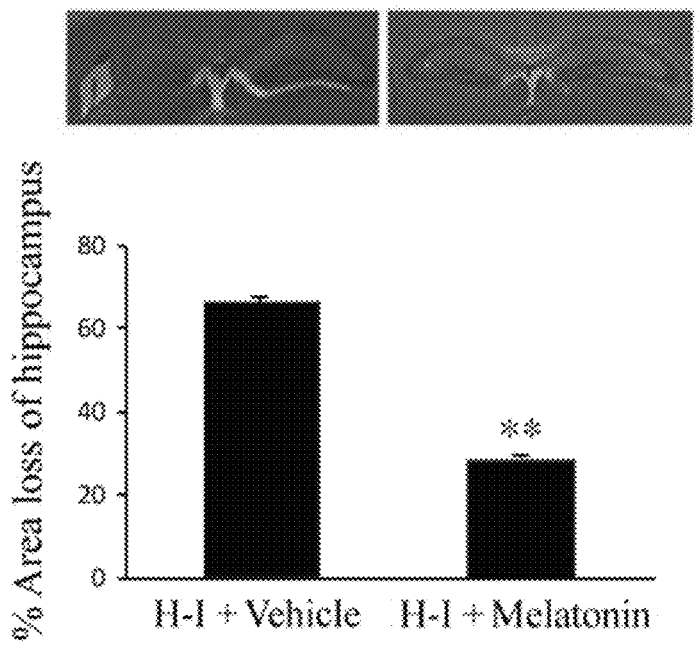

Example 4. Melatonin Reduces Brain Damage in Neonatal Hypoxic-Ischemic Mice in Vivo To investigate the long-term effect of administration of melatonin in reducing brain injury in neonatal H-I brain injury model, animals were euthanized 7 days after H-I injury and evaluated for histological damage with H & E staining (FIG. 9A, 9B). There was significant reduction in percentage brain tissue loss in the brain hemisphere ipsilateral to carotid ligation compared to the uninjured contralateral hemisphere in melatonin treated pups (9.7%) compared to vehicle treated group (24.6%) (FIG. 9A). Since the hippocampus is a highly vulnerable area for H-I brain injury, we further evaluated the neuroprotection of melatonin in H-I brain injury specific to hippocampus damage. The data showed that H-I injury caused significant area loss in hippocampus (66.5%) in the brain ipsilateral to carotid ligation, while melatonin treatment significantly reduced the size of the hippocampal tissue loss (28.6%) (FIG. 9B).

Figure 9C:
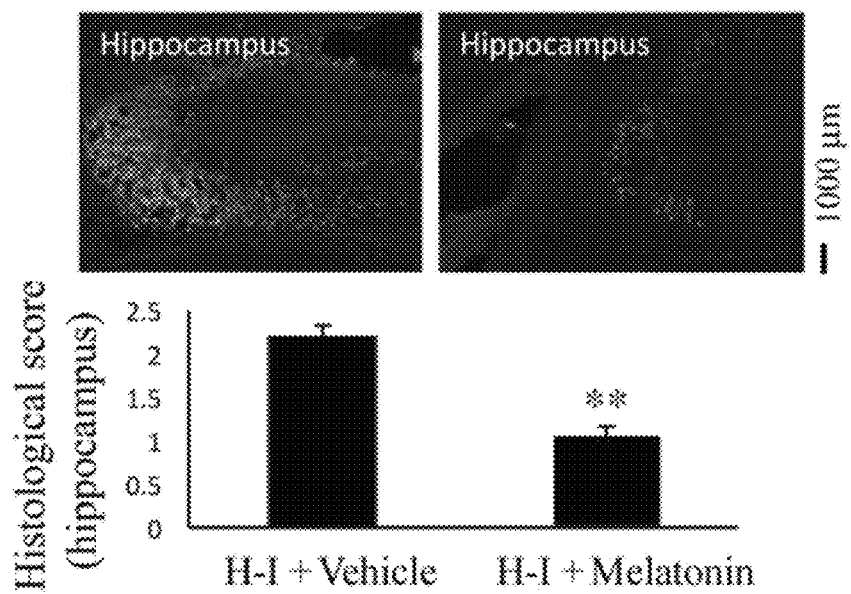
Figure 9D:
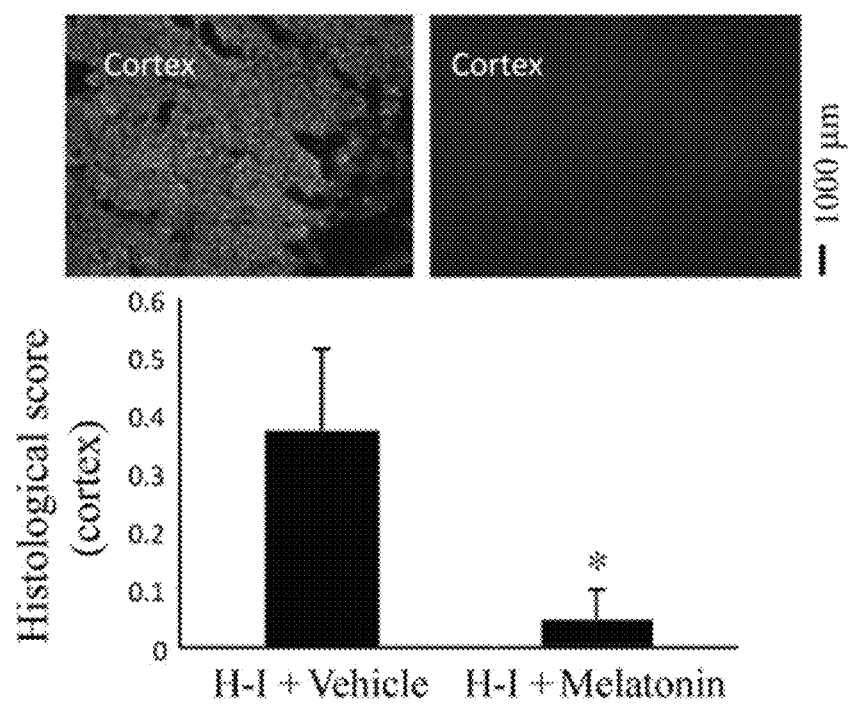

To investigate the protective mechanisms of melatonin against H-I brain injury, we examined whether melatonin administration reduces cell death in neonatal H-I mice in the short-term. At 48 hr of life, the pups were euthanized and neuronal cell death was evaluated with FJB staining (FIG. 9C, 9D). Fluoro-Jade-B (FJB) stain mainly identifies areas of neuronal injury, predominantly degenerating neurons, and is widely used for histological staining of neurons undergoing neurodegeneration and provides a neuronal cell death marker. Hypoxia-ischemia caused significant damage in not only hippocampus but also cortex in the brain ipsilateral to carotid ligation. FJB staining indicated dramatically more positive cells in the hippocampus (FIG. 9C, upper panel) and cortex (FIG. 9D, upper panel) in brain sections of vehicle treated group compared with melatonin treated group of pups. Furthermore, the neurological score assigned by evaluating the FJB positive cells in the hippocampus (FIG. 9C, lower panel) and cortex (FIG. 9D, lower panel) showed significantly higher score (representing worse damage) in vehicle treated pups compared with melatonin treated pups. Thus we have demonstrated that melatonin reduces long term brain loss at 7 days as well as short term neuronal cell death at 48 hr in neonatal H-I mice in vivo.

Example 5. N-Acetylserotonin (NAS) in ALS

Figure 10:
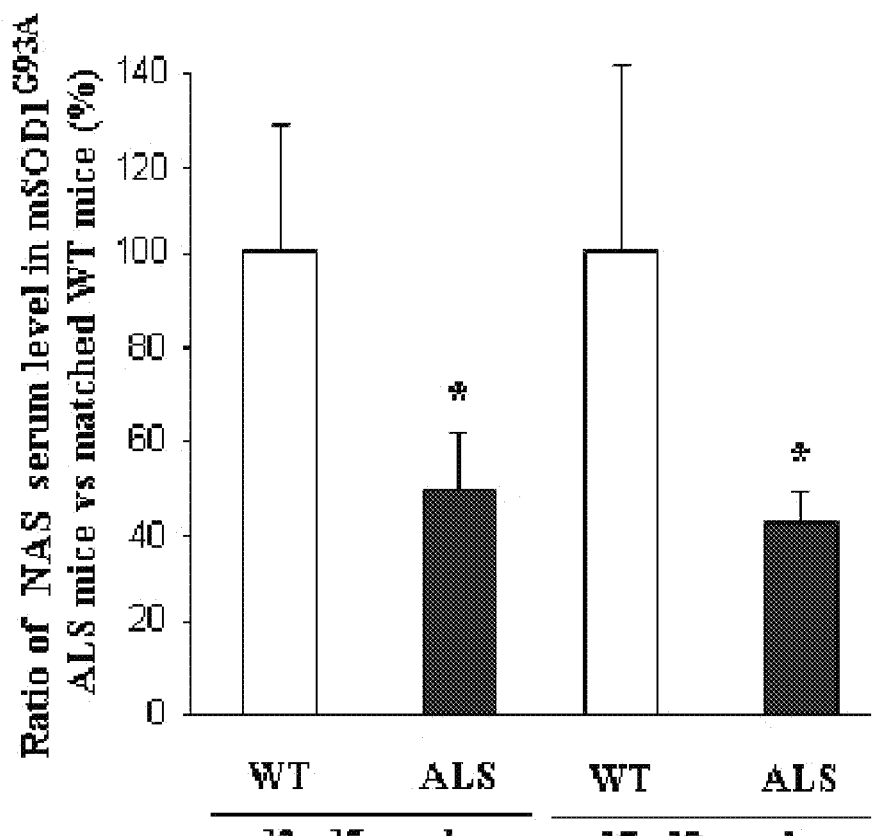
FIG. 10. NAS serum levels were lower in ALS mice. Serum samples (100 ml) from ALS and WT mice were collected. Cold methanol was added, followed by centrifugation at 14,000 rpm for 15 mins. The supernatant was collected and tested by Liquid chromatography-mass spectrometry (LC/MS) in the FAS Center for Systems Biology, Harvard University. The corresponding peak area was recorded, and the concentration of NAS in the blood samples was calculated by standard positive controls. n=4-6 for 13-15 weeks and n=10-12 for 17-19 weeks (C). * p<0.05.

To evaluate the role of NAS in ALS, serum samples (100 ml) from ALS and WT mice were collected. Cold methanol was added, followed by centrifugation at 14,000 rpm for 15 mins. The supernatant was collected and tested by Liquid chromatography-mass spectrometry (LC/MS) in the FAS Center for Systems Biology, Harvard University. The corresponding peak area was recorded, and the concentration of NAS in the blood samples was calculated by standard positive controls. As shown in FIG. 10, NAS serum levels were lower in ALS mice.

Figure 11:
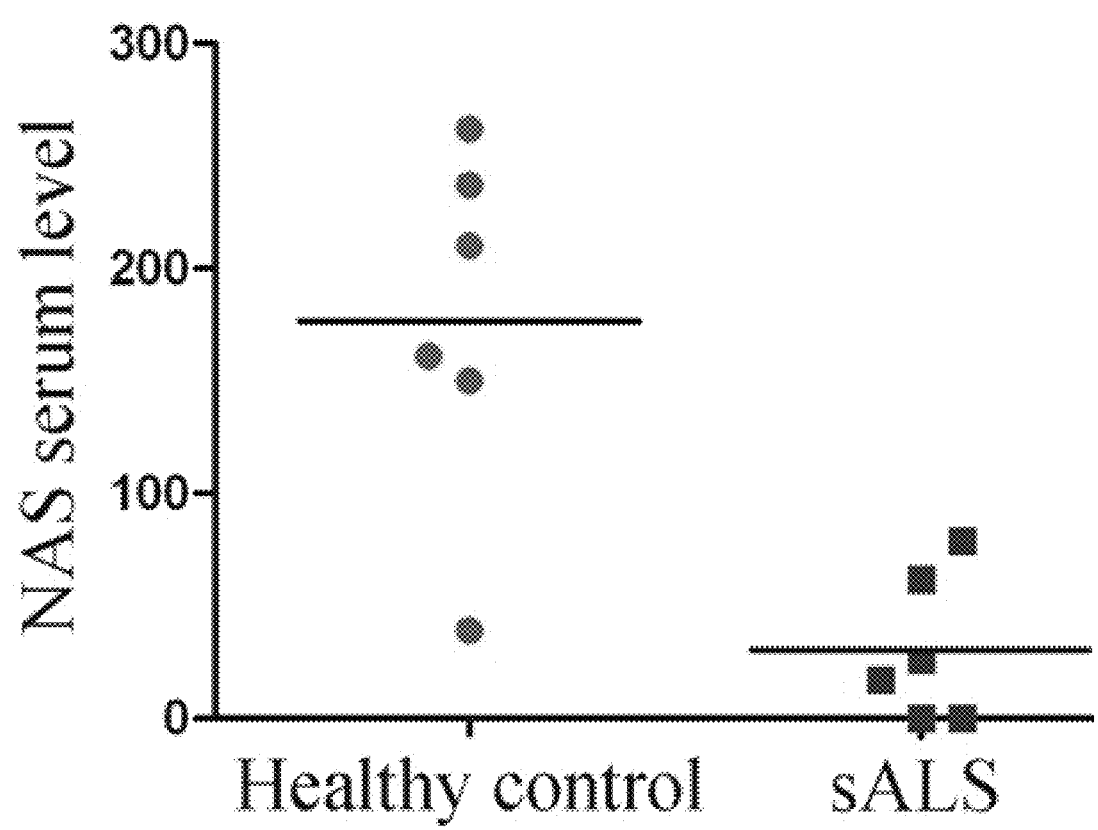
FIG. 11. NAS was reduced in the serum samples of sALS patients. Blood samples were collected from sALS patients (n=6) and healthy controls (n=6) at 8-10 am. The concentration of NAS were measured by LC/MS assay. Scatter plot graph presented the data from healthy subjects and sALS patients group. The average 176.5 in the healthy control group and 30.7 in the ALS group, which showed a 5.8 folds of reduction. The sensitivity (83%) and specificity (100%) of NAS assay were calculated.

In addition, blood samples were collected from sALS patients (n=6) and healthy controls (n=6) at 8-10 am. The concentration of NAS were measured by LC/MS assay. As shown in FIG. 11, NAS was reduced in the serum samples of sALS patients. The average was 176.5 in the healthy control group and 30.7 in the ALS group, which showed a 5.8 fold reduction. The sensitivity (83%) and specificity (100%) of NAS assay were calculated.

Figure 12:
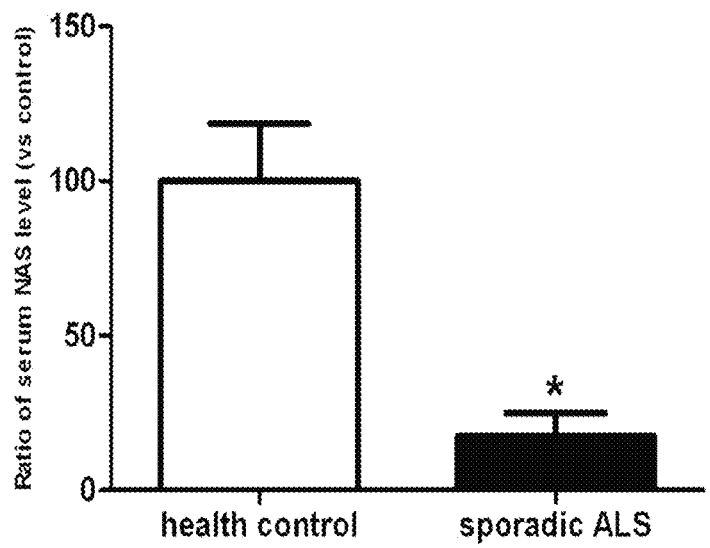
FIG. 12 NAS levels were lower in serum samples from sporadic ALS patients. Serum samples (100 ml) from human ALS patients (n=6) and healthy control subjects (n=6) were collected. Cold methanol was added, followed by centrifugation at 14,000 rpm for 15 mins. The supernatant was collected and tested by LC/MS in the FAS Center for Systems Biology, Harvard University. The corresponding peak area was recorded, and the concentration of endogenous NAS in the blood samples was calculated by standard positive controls. Examples of NAS positive control (200 fg/ml NAS), endogenous NAS secretion in the serum sample of human healthy subjects and sporadic ALS patients were shown. Data were presented as mean±SEM. p<0.05 (t-test).
Figure 12:
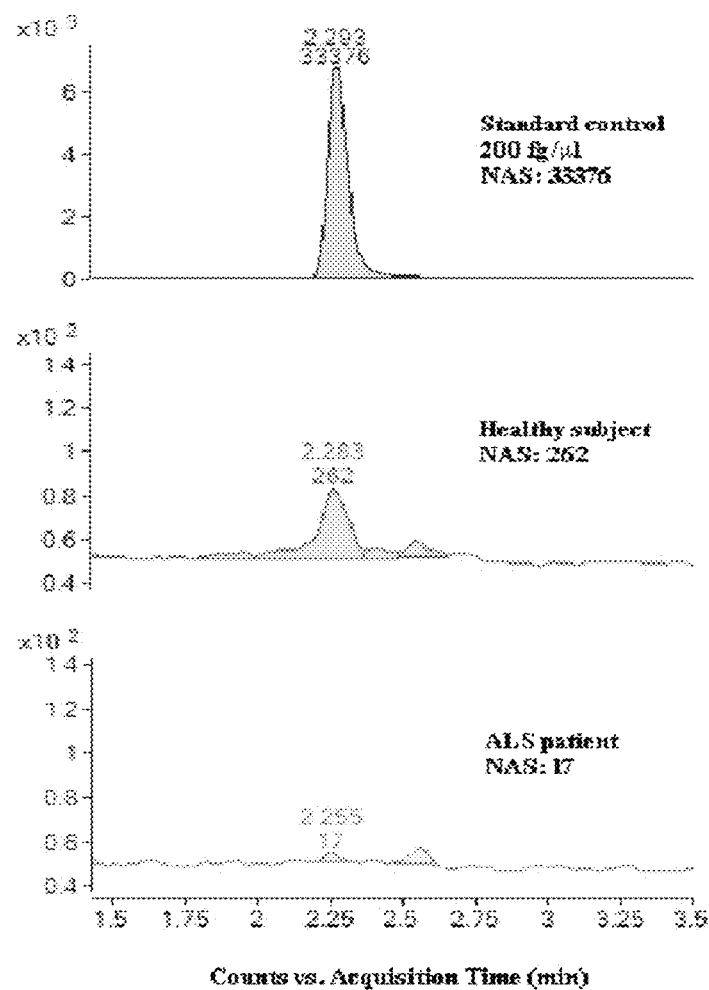

Serum samples (100 ml) from human ALS patients (n=6) and healthy control subjects (n=6) were collected. Cold methanol was added, followed by centrifugation at 14,000 rpm for 15 mins. The supernatant was collected and tested by LC/MS in the FAS Center for Systems Biology, Harvard University. The corresponding peak area was recorded, and the concentration of endogenous NAS in the blood samples was calculated by standard positive controls. Examples of NAS positive control (200 fg/ml NAS), endogenous NAS secretion in the serum sample of human healthy subjects and sporadic ALS patients are shown in FIG. 12, showing that NAS levels were lower in serum samples from sporadic ALS patients.

Figure 13A:
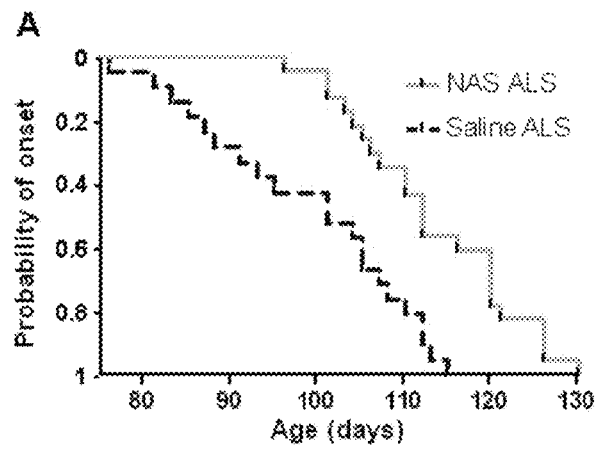
FIGS. 13A-13B. NAS delays disease onset and mortality in mSOD1 G93A mice. Administration of 15 mg/kg/day NAS by daily IP injection initiated at 6 weeks old age delays ALS disease onset defined as being failed to pass the rotarod task at 15 rpm (A), and protects ALS mice by extending survival (B).
Figure 13B:
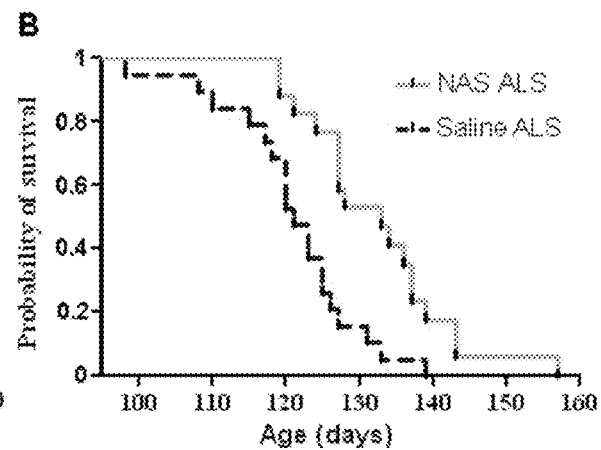
Figure 14A:
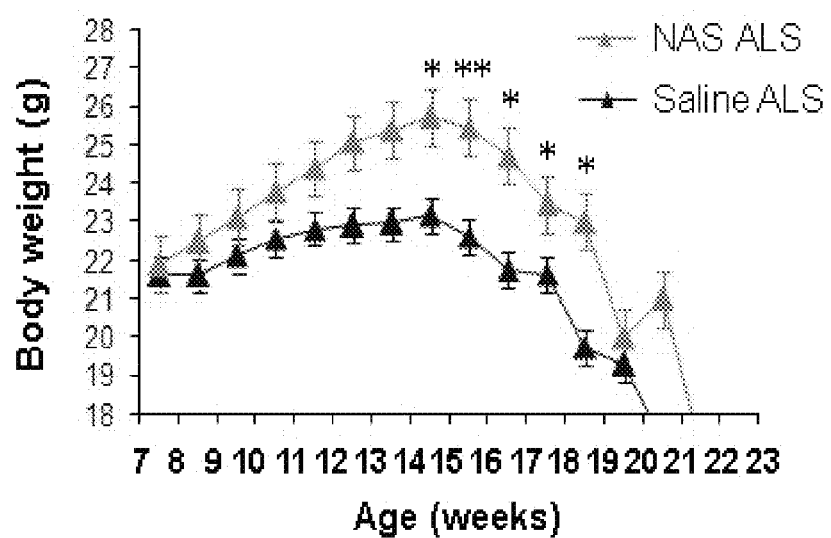
FIGS. 14A-14B. NAS treatment prevents the loss of body weight during the development of pathogenesis in mSOD1 G93A mice but not in WT mice. Administration of 15 mg/kg NAS (A, B) or 7.5 mg/kg (B), 30 mg/kg (B), 45 mg/kg (B), by daily IP injection started at 6 weeks, prevents the loss of body weight in mSOD1 G93A mice (A) but NAS has no effect on body weight in WT mice (B). Data were presented as mean±SEM. * p<0.05, ** p<0.01 compared with saline ALS group.
Figure 14B:
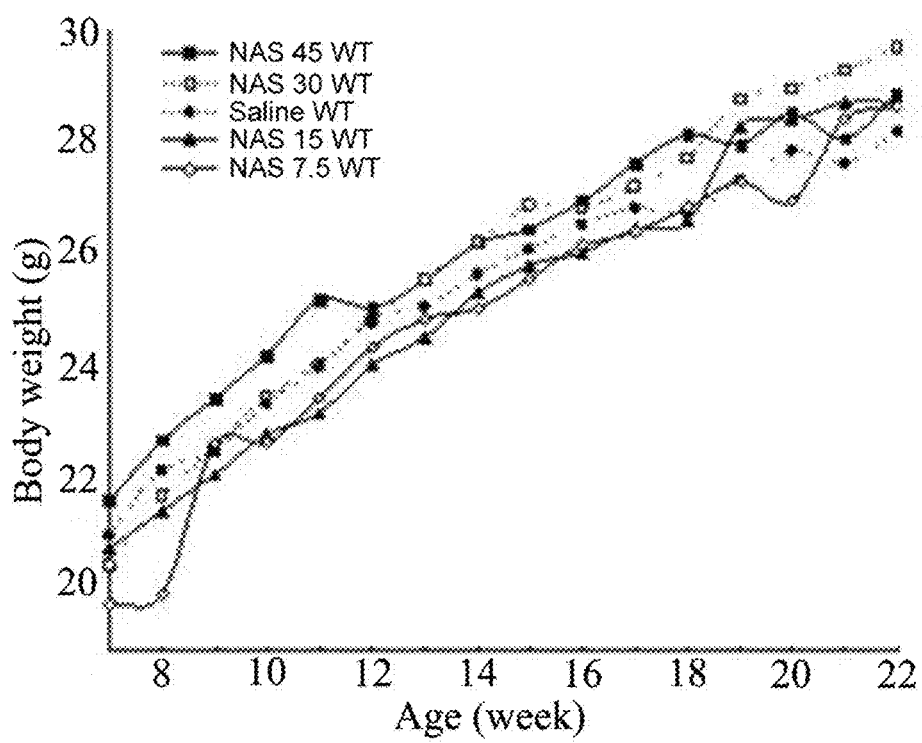
Figure 15:
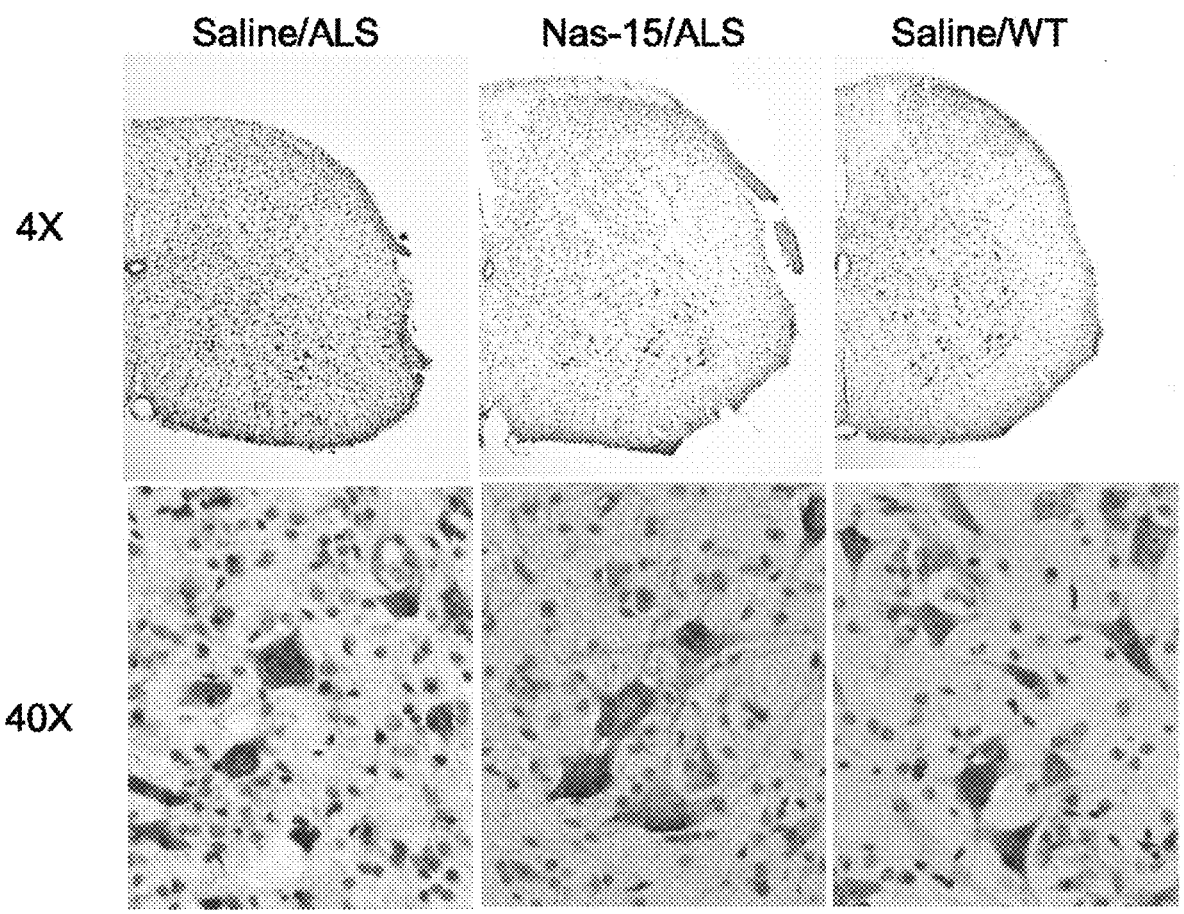
FIG. 15. NAS prevents the motor neuron loss in mSOD1 G93A ALS mice. ALS mice treated with saline as vehicle shows loss of motor neurons in lumbar spinal cord, whereas treatment of NAS can ameliorate the loss of motor neurons (Nissl staining).

To determine whether NAS could be used therapeutically in these subjects, NAS was administered at 15 mg/kg/day by daily IP injection initiated at 6 weeks of age. As shown in FIG. 13A, NAS administration delayed disease onset and mortality in mSOD1 G93A mice. ALS disease onset was defined as failure to pass the rotarod task at 15 rpm. NAS also protected ALS mice by extending survival (see FIG. 13B). In addition, as shown in FIGS. 14A-14B, NAS treatment prevented the loss of body weight during the development of pathogenesis in mSOD1 G93A mice but not in WT mice. Administration of 15 mg/kg NAS (14A, 14B) or 7.5 mg/kg (14B), 30 mg/kg (14B), 45 mg/kg (14B), by daily IP injection started at 6 weeks, prevents the loss of body weight in mSOD1 G93A mice (14A) but NAS has no effect on body weight in WT mice (14B). As shown in FIG. 15, ALS mice treated with saline as vehicle showed loss of motor neurons in lumbar spinal cord, whereas treatment of NAS can ameliorate the loss of motor neurons (Nissl staining). Thus NAS administration also prevents motor neuron loss in mSOD1 G93A ALS mice.

These results are similar to those seen in cerebral ischemia, in which NAS administration has been shown to diminish lesion size, improve neurological score, and attenuate neuronal cell death; see Zhou et al., Journal of Neuroscience, 34(8):2967-2978 (2014).

Example 6. Serotonin Levels in HIE

Figure 16:
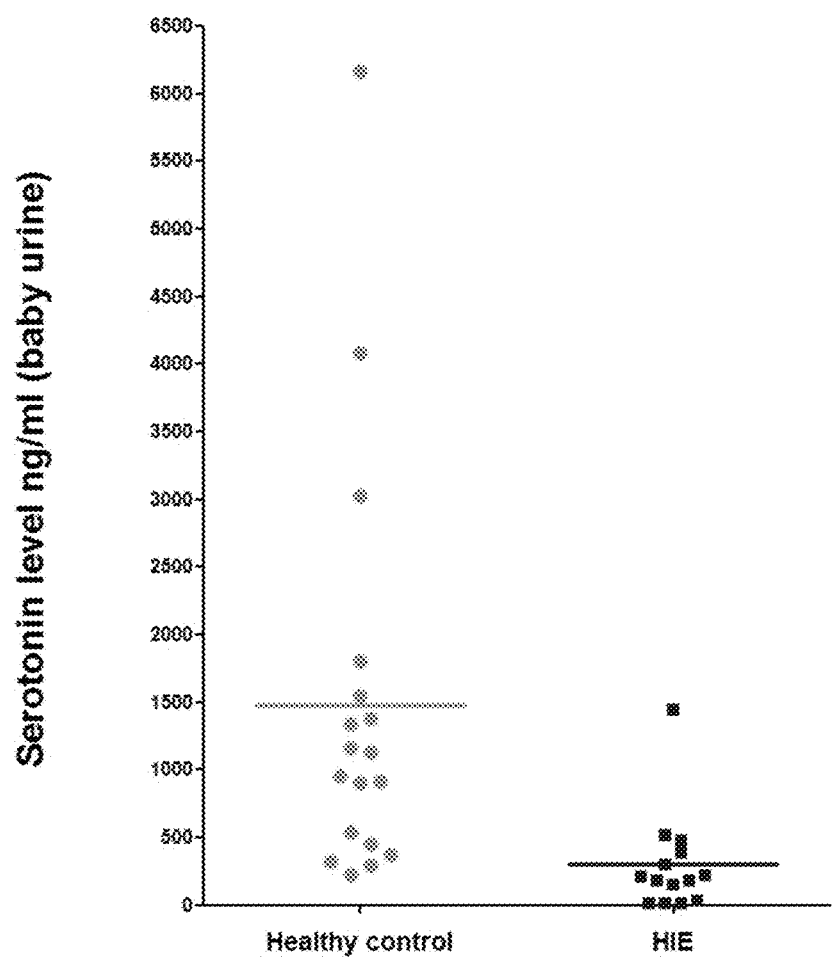
FIG. 16. Serotonin urine levels were reduced in HIE patients. Urine samples were collected from HIE patients (n=14), healthy controls (n=18). The levels of urine serotonin were measured by human serotonin ELISA kit. Scatter plot graphs presented the concentrations of urine serotonin.

To evaluate serotonin levels in newborn HIE, urine samples were collected from HIE patients (n=14), healthy controls (n=18). The levels of urine serotonin were measured by human serotonin ELISA kit. As shown in FIG. 16, serotonin urine levels were reduced in HIE patients.

Table 3 presents a comparison of serotonin cord blood levels with Apgar score, cord pH/baby pH, EEG and MRI, and days of hospitalization in HIE patients and healthy subjects. All of the infants were Inborn. No EEG or MRI was obtained for the Healthy subjects, while EEG and MRI were abnormal in both HIE subjects.

TABLE 3

Comparison of serotonin cord blood levels with clinical short-term outcomes in newborn HIE patients

| Study ID | Serotonin (ng/ml) | Apgar score 1, 5, 10 min | Cord pH | Baby pH | Days of hospitalization | GA (week) | BW (g) | Mode of delivery | Gender |
|---|---|---|---|---|---|---|---|---|---|
| Healthy No. 3 | 242.8 | 9, 9, 9 | — | — | 2 | 40.3 | 3460 | CS | Female |
| Healthy No. 4 | 176.6 | 8, 9, 9 | — | — | 4 | 38.8 | 3016 | CS | Male |
| HIE No. 1 | 23.4 | 2, 2, 4 | — | 7.30 | 4 | 37.3 | 2679 | CS | Male |
| HIE No. 2 | 22.4 | 2, 5, 7 | 6.95 | 7.17 | 12 | 39.0 | 3320 | CS | Male |

Gestational age (GA); body weight (BW); mode of delivery, VD = Vaginal Delivery.
CS = Cesarean Section

Example 7. Serotonin Levels in Amyotrophic Lateral Sclerosis (ALS)

Figure 17:
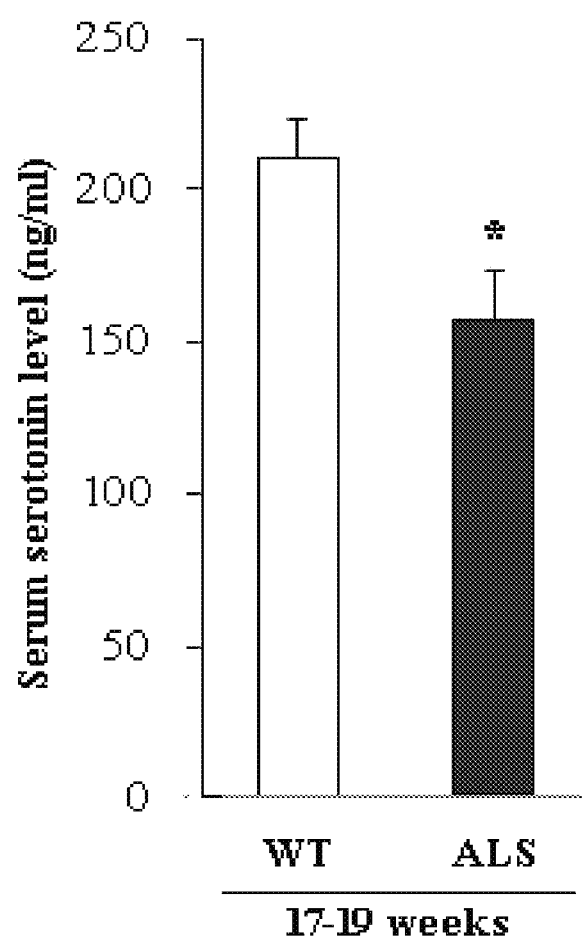
FIG. 17. Serotonin serum levels were lower in ALS mice. Serum samples (100 ml) from end-stage of ALS and matched WT mice were collected at 8-9 am. Serum samples (100 ml) were submitted for serotonin ELISA measurement. N=4 for 17-19 weeks of mice. * p<0.05.

Serum samples (100 ml) from end-stage of ALS and matched WT mice were collected at 8-9 am. Serum samples (100 ml) were submitted for serotonin ELISA measurement. As shown in FIG. 17, serotonin serum levels were lower in the ALS mice.

Figure 18:
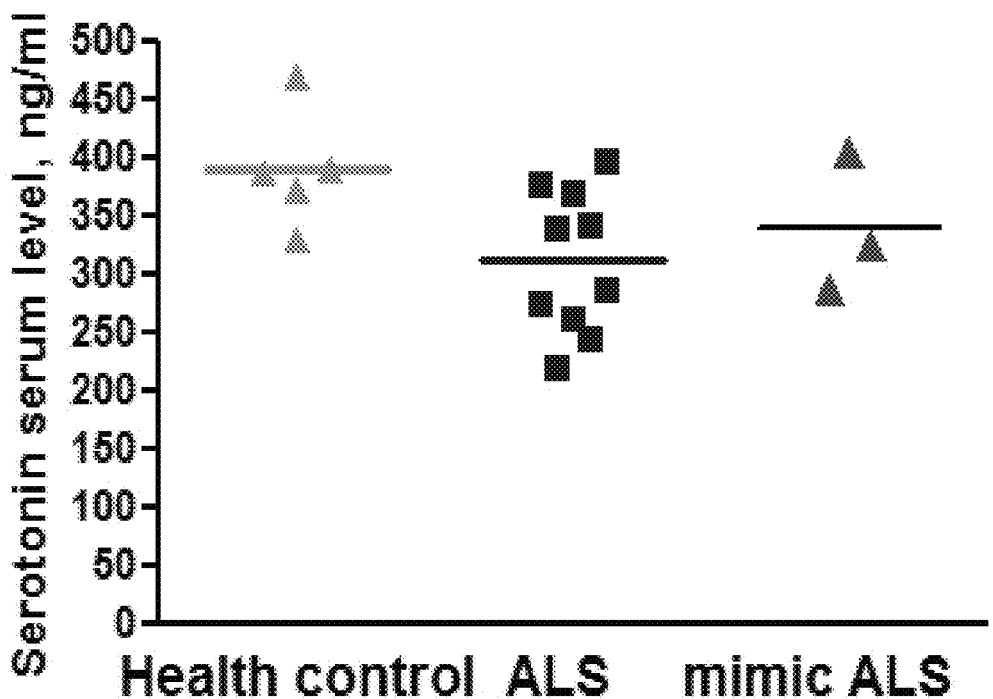
FIG. 18. Serotonin blood levels were reduced in early sALS patients. Blood samples were collected from sALS patients (blue, n=10), healthy controls (green, n=5), and mimic ALS (red, n=3). The levels of serum serotonin were measured by human serotonin ELISA kit. Scatter plot graphs presented the concentrations of serum serotonin.

Blood samples were also collected from sALS patients, healthy controls, and mimic ALS. The levels of serum serotonin were measured by human serotonin ELISA kit. As shown in FIG. 18, serotonin blood levels were also reduced in early sALS patients.

Example 8. 5-Hydroxytryptophan (5-HTP) and Tryptophan Levels in HIE and ALS

Figure 19:
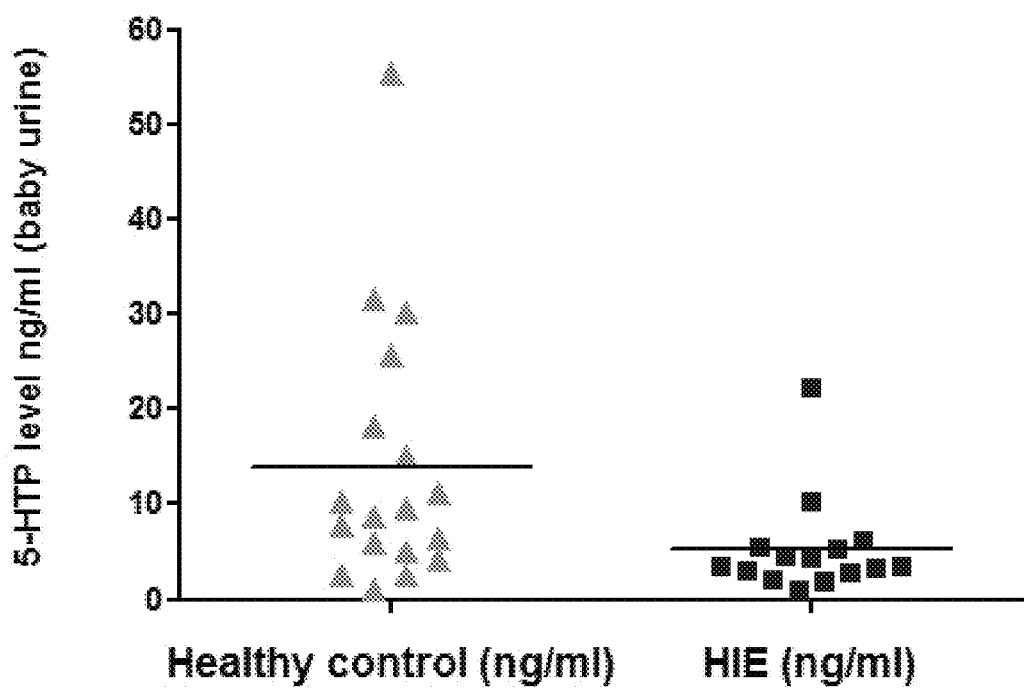
FIG. 19. 5-HTP urine levels were reduced in HIE patients. Urine samples were collected from HIE patients (blue, n=15), healthy controls (green, n=18). The levels of urine serotonin were measured by human 5-HTP ELISA kit. Scatter plot graphs presented the concentrations of urine 5-HTP.

Urine samples were collected from HIE patients and healthy controls. The levels of urine 5-HTP were measured by human 5-HTP ELISA kit. As shown in FIG. 19, 5-HTP urine levels were reduced in HIE patients.

Figure 20:
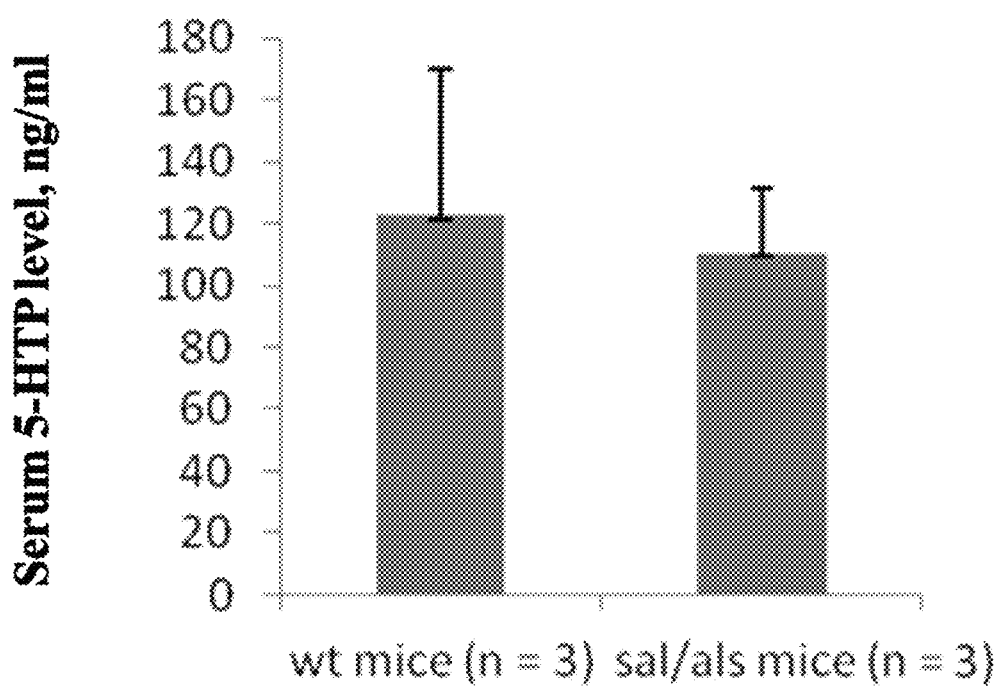
FIG. 20. 5-HTP blood levels in end-stage of ALS mice. Blood samples from mSOD1$^{G93A}$ mice (n=3) and WT littermates at 17-19 weeks (n=3) were collected at 8-9 am. Serum samples (100 ml) were submitted for 5-HTP ELISA measurement.

Blood samples were also collected from mSOD1G93A mice and WT littermates at 17-19 weeks at 8-9 am. Serum samples were submitted for 5-HTP ELISA measurement. As shown in FIG. 20, 5-HTP blood levels were reduced in end-stage of ALS mice.

Figure 21:
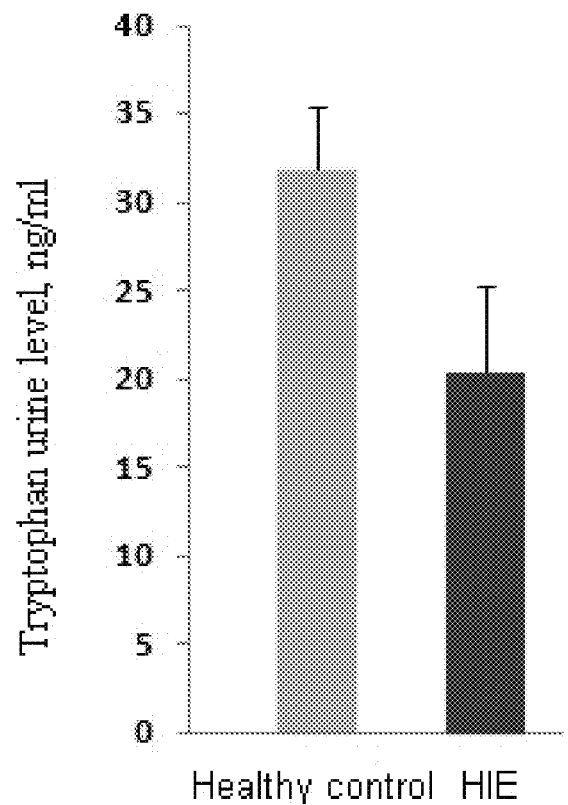
FIG. 21. Tryptophan levels were reduced in baby urine samples of HIE compared with control subjects. Baby urine samples were collected from healthy subjects (n=11, green) and HIE (n=8, blue). The samples were tested by tryptophan ELISA kit. Measured samples were quantified by standard curves to obtain the concentration of targeting tryptophan. Data were presented as mean±SEM. p=0.08 (t-test).

Baby urine samples were also collected from healthy subjects and HIE. The samples and tested by tryptophan ELISA kit. As shown in FIG. 21, tryptophan levels were reduced in baby urine samples of HIE compared with control subjects.

Figure 22:
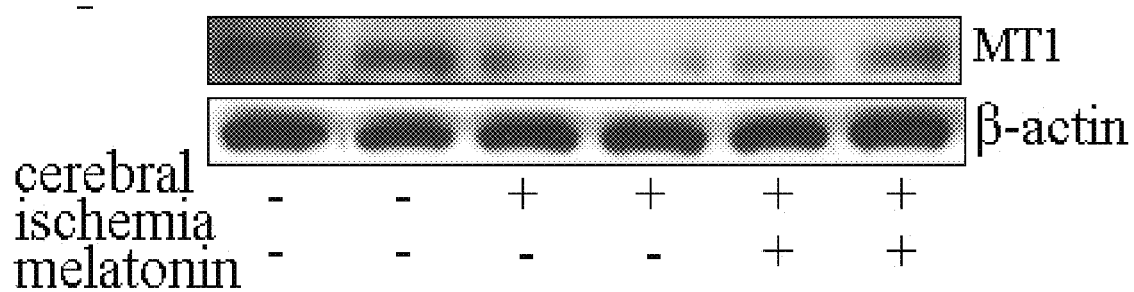
FIG. 22. Western blot analysis of expression of melatonin receptor 1A in MCAO mice. Protein samples from brains of MCAO mice with saline or melatonin and vehicle control mice were obtained. Different groups of mice were comprised of equal (or nearly equal) numbers of males and females. Protein samples were analyzed for the expression of MT1 proteins using MT1 antibody with b-actin as the internal control. MT1 was lost/reduced in MCAO) mice and the administration of melatonin restores its deficiency.

Example 9. Western Blot Analysis of Expression of Melatonin Receptor 1A (MT1) in MCAO Mice Protein samples from brains of MCAO mice with saline or melatonin and vehicle control mice were obtained. Different groups of mice were comprised of equal (or nearly equal) numbers of males and females. Protein samples were analyzed for the expression of MT1 proteins using MT1 antibody with b-actin as the internal control. The results are shown in FIG. 22. MT1 was lost/reduced in MCAO) mice and the administration of melatonin restored its deficiency.

Example 10. Expression of Melatonin Receptor 1A (MT1) in ALS

Figure 23:
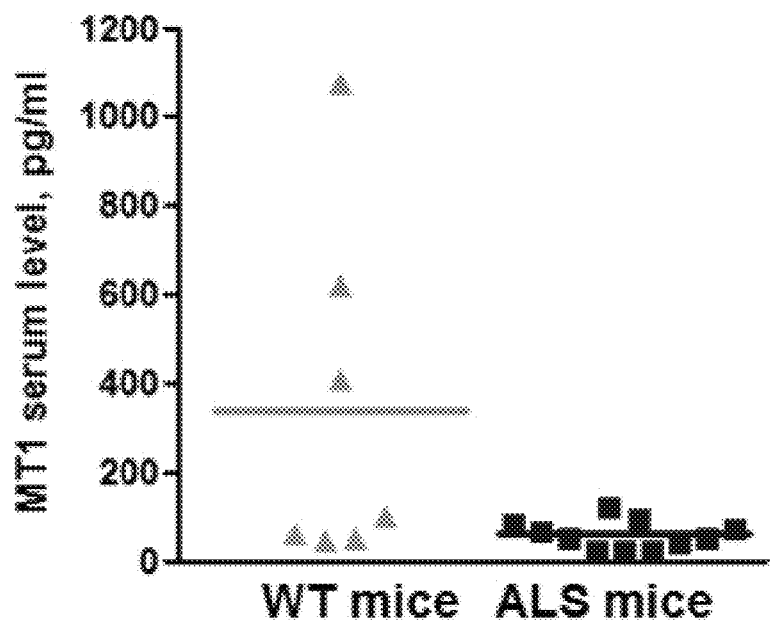
FIG. 23. Comparison of MT1 blood levels in mSOD1G$^{93A}$ mice. Blood samples were collected in 17-19 weeks of mSOD1$^{G93A}$ ALS mice (n=9) and WT littermates (n=6). Serum samples were submitted for mouse MT1 ELISA measurement. Scatter plot graph was performed by the GraphPad Prism program and Horizontal line represents the median (through whole proposal).

Blood samples were collected in 17-19 weeks of mSOD1$^{G93A}$ ALS mice (n=9) and WT littermates (n=6). Serum samples were submitted for mouse MT1 ELISA measurement. FIG. 23 shows the results of a comparison of MT1 blood levels in mSOD1G93A mice with normal mice, demonstrating a significant reduction in serum Mt1 levels in the ALS mice.

Figure 24:
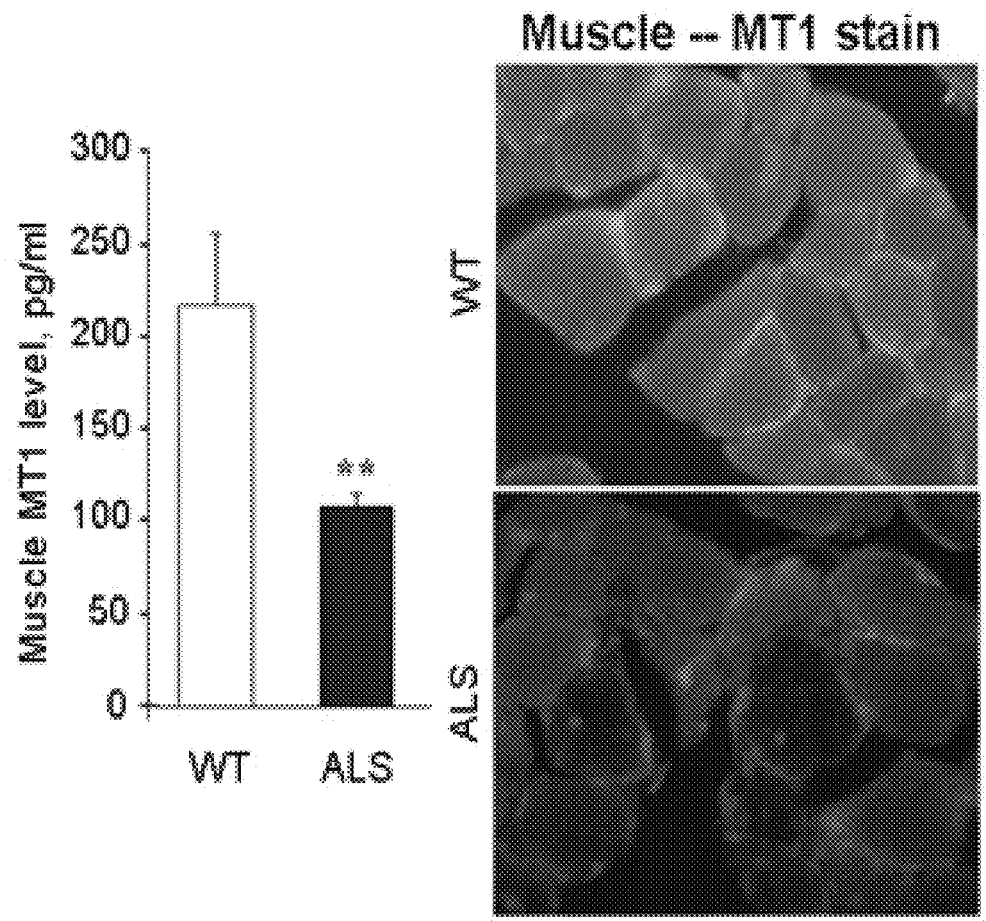
FIG. 24. MT1 was diminished in muscle during ALS progression. ALS mice in late-stage ALS (17-18 weeks) and WT littermates were sacrificed. Gastrocnemius in the hindlimb of mSOD1$^{G93A}$ mice and WT littermates were extracted to obtain lysate for ELISA assay (left panel) or dissected, postfixed and the frozen sections (18 μm) were immunstained with MT1 antibodies (right panel). Statistical significance was evaluated by t test: **p<0.01.

ALS mice in late-stage ALS (17-18 weeks) and WT littermates were sacrificed. Gastrocnemius in the hindlimb of mSOD1$^{G93A}$ mice and WT littermates were extracted to obtain lysate for ELISA assay or dissected, postfixed and the frozen sections were immunstained with MT1 antibodies. As shown in FIG. 24, FIG. 24. MT1 was diminished in muscle during ALS progression.

Figure 25A:
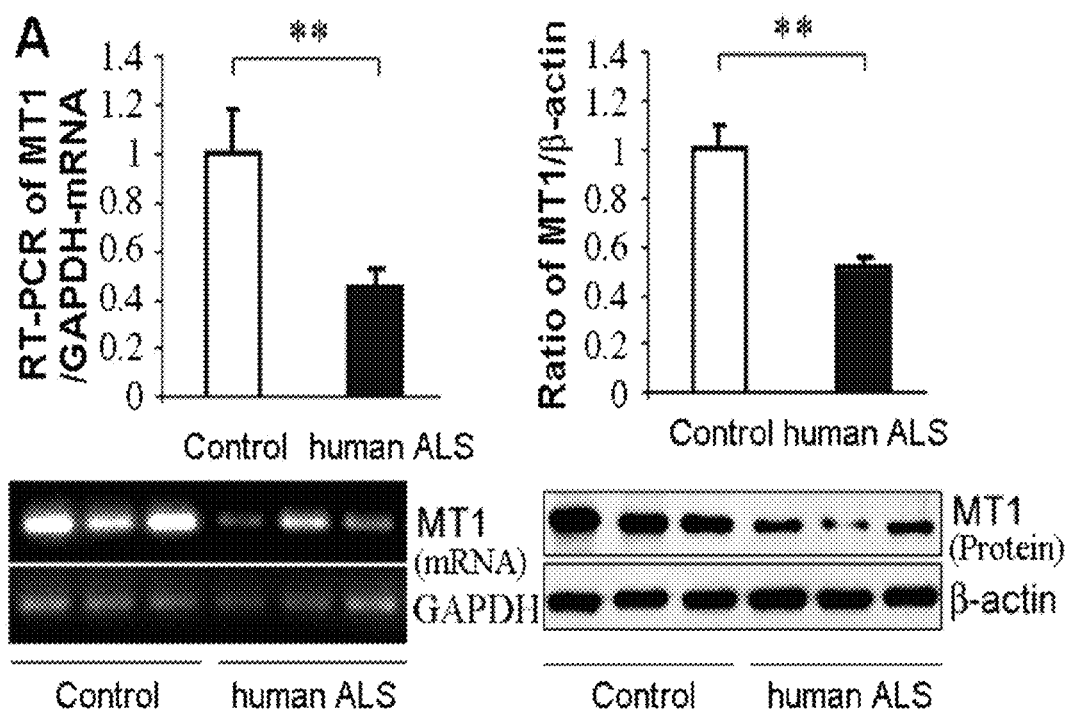
FIGS. 25A-25B. MT1 Levels were lower in ALS patients than in persons who died of non-neurologic causes. Human samples were obtained from the lumbar spinal cord of ALS patients (average age 61.0 years and average postmortem interval 4.6 h, n=5-6) and control samples from non-neurologic patients (average age 59.5 years and average postmortem interval 8.5 h, n=5-6) from our collaborator Northeast ALS Consortium Chair Robert Bowser. Spinal cord samples were analyzed for the expression of MT1 mRNAs and proteins with GAPDH and b-actin as the internal control, respectively (A). The human-specific primers used for RT-PCR were those described previously. Statistical significance was evaluated by t test. MT1 immunostaining (green) with MT1 antibodies and DAPI (4',6-diamidino-2-phenylindole) staining (blue) in the lumbar regions of spinal cords were performed in sections of lumbar regions of spinal cord from non-neurologic patients and ALS patients (obtained from SACTL-VA Biorepository Trust) (B, n=5). An example of immunostaining shows MT1 primarily locates in motor neurons. MT1 positive motor neuron was counted under fluorescent microscopy and compared between ALS and control subjects (B).
Figure 25B:
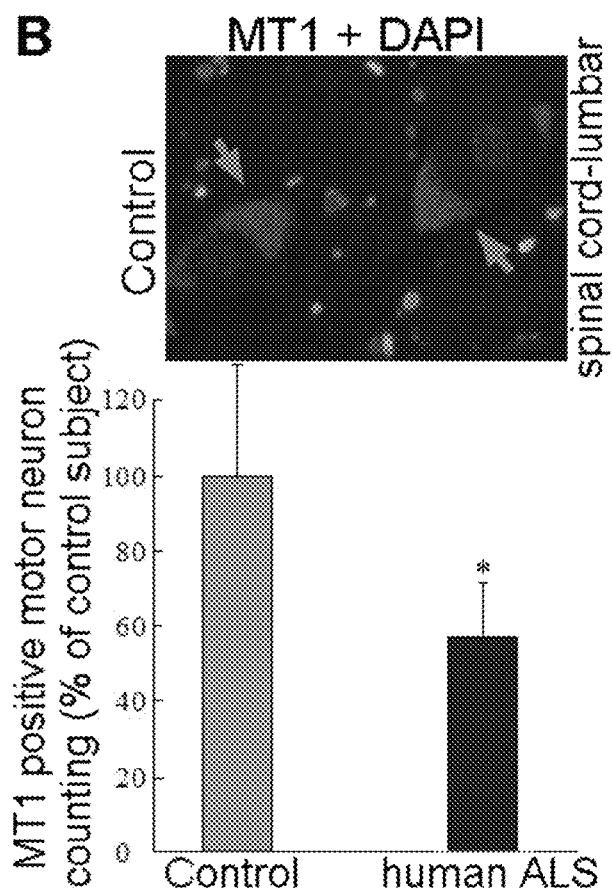

Human samples were obtained from the lumbar spinal cord of ALS patients (average age 61.0 years and average postmortem interval 4.6 h, n=5-6) and control samples from non-neurologic patients (average age 59.5 years and average postmortem interval 8.5 h, n=5-6) from our collaborator Northeast ALS Consortium Chair Robert Bowser. Spinal cord samples were analyzed for the expression of MT1 mRNAs and proteins with GAPDH and b-actin as the internal control, respectively. The human-specific primers used for RT-PCR were 5'-TGCTACATCTGCCACA-GTCTC-3' (SEQ ID NO:5) and 5'-CAGTAGCCCG-TATATAATGGC-3' (SEQ ID NO:6). Statistical significance was evaluated by t test. MT1 immunostaining with MT1 antibodies and DAPI (4',6-diamidino-2-phenylindole) staining in the lumbar regions of spinal cords were performed in sections of lumbar regions of spinal cord from non-neurologic patients and ALS patients (obtained from SACTL-VA Biorepository Trust). Immunostaining showed that MT1 primarily locates in motor neurons. MT1 positive motor neurons were counted under fluorescent microscopy and compared between ALS and control subjects. As shown in FIGS. 25A-25B, MT1 Levels were lower in ALS patients than in persons who died of non-neurologic causes.

Figure 26:
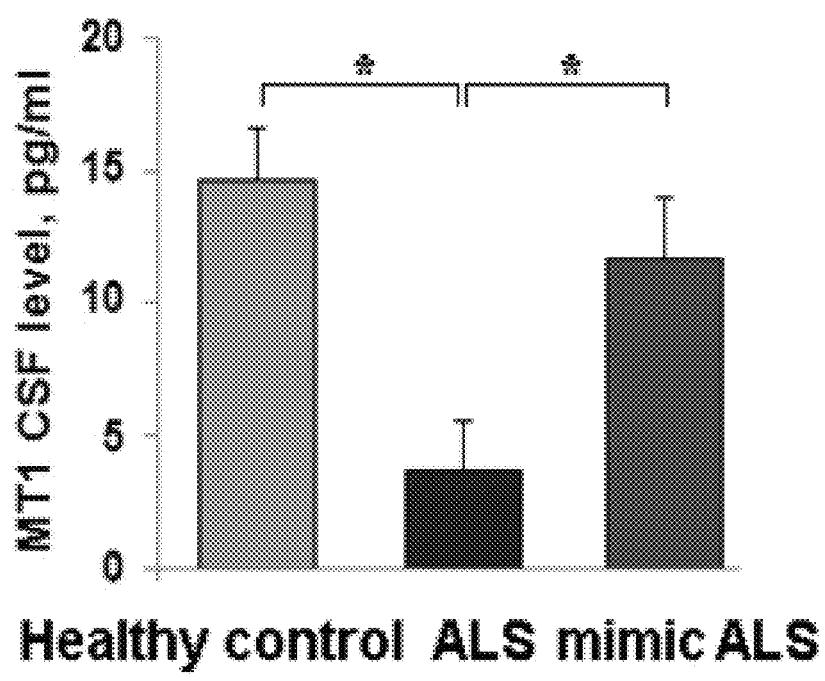
FIG. 26. Comparison of MT1 CSF levels in sALS patients. CSF samples were collected at 8-10 am from sALS patients (n=4, blue), mimic ALS patients (n=3, red), and healthy controls (n=3, green). The concentrations of MT1 were measured by human MT1 ELISA kit. MT1 levels were shown.
Figure 27:
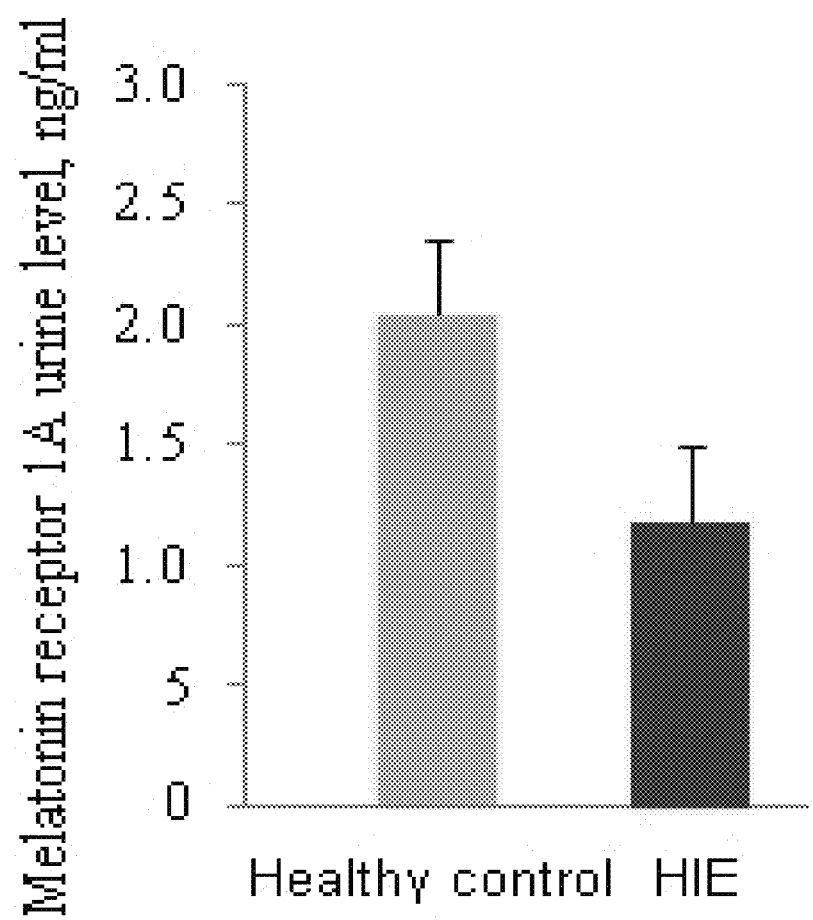
FIG. 27. MT1 levels were lower in urine samples of HIE than in control subjects. Urine samples were collected from healthy subjects (green, n=12) and HIE (blue, n=8) and tested by MT1 ELISA kit. Measured samples were quantified by standard curves to obtain the concentrations of targeting MT1. Data were presented as mean+SEM. p=0.07 (t-test).

In addition, CSF samples were collected at 8-10 am from sALS patients (n=4), mimic ALS patients (n=3), and healthy controls (n=3). The concentrations of MT1 were measured by human MT1 ELISA kit. FIG. 26 shows that MT1 CSF levels were significantly lower in sALS patients.

Example 11. Expression of Melatonin Receptor 1A (MT1) in HIE

Urine samples were collected from healthy subjects (green, n=12) and HIE (blue, n=8) and tested by MT1 ELISA kit. Measured samples were quantified by standard curves to obtain the concentrations of targeting MT1. As shown in FIG. 26, MT1 levels were lower in urine samples of HIE than in control subjects.

Figure 28A:
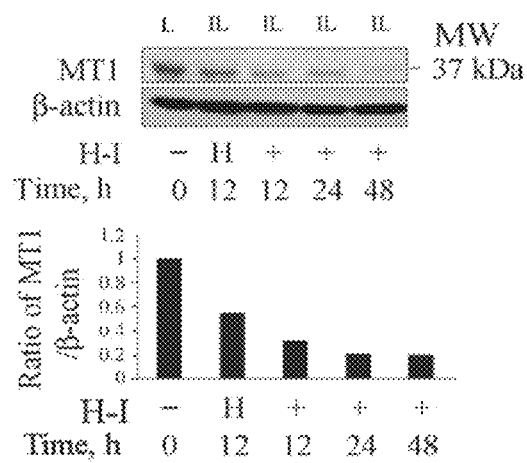
FIGS. 28A-28D. Reduced MT1 expression with hypoxia-ischemia and increased mortality in MT1 −/− pups. Postnatal day 8 mice underwent unilateral carotid ligation followed by 60 min of hypoxia. The administration of melatonin 10 mg/kg or 3% Tween was performed 30 min prior to hypoxia-ischemia (H-I) or treated with hypoxia alone without preceding ischemia (H). Mice were sacrificed at 12 (A), 24 (A, B) and 48 hr (A, C) post H-I injury. Brains were obtained and cytosolic fractions or total lysates were extracted and then analyzed by western blotting using antibodies to MT1 with 3-actin as a loading control. Each lane pair in these representative western blots represents a different mouse with ipsilateral (IL) and contralateral (CL) brain hemispheres. The bar graphs show the quantitative densitometry analysis of western blots. Control pups (n=9), H-I pups at 24 hr (n=6), H-I pups at 48 hr (n=3), and H-I pups at 48 hr pretreated with melatonin (n=3). *p<0.05, p<0.01, control vs. H-I injured mice. MT1 KO mice were subjected to unilateral carotid ligation followed by hypoxia (D) and mortality were calculated in 5 litters of MT1 −/− pups compared to 5 litters of C57BL6-wild type pups. The data were presented as mean±SEM. p<0.01. L: control brain, left side, R: control brain, right side, CL=contralateral brain, IL=ipsilateral brain to H-I injury.
Figure 28B:
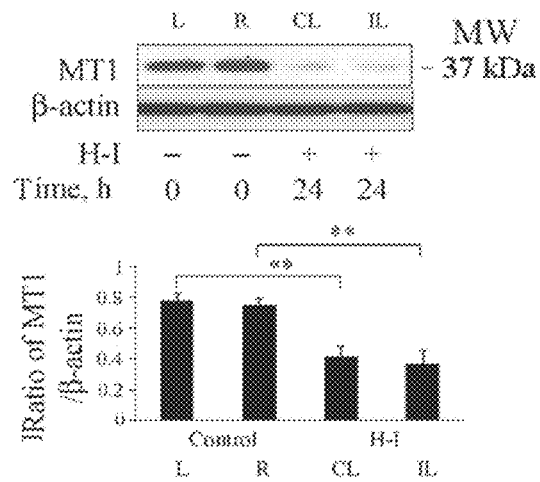
Figure 28C:
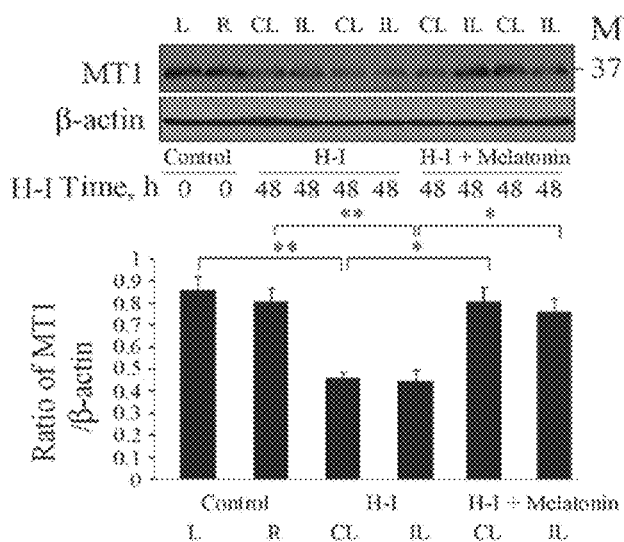

Example 12. MT1 is Reduced in Damaged Brain of Neonatal Hypoxic-Ischemic Mice In Vivo, while Melatonin Inhibits the MT1 Deficiency In order to investigate whether the expression of MT1 is reduced in H-I brain tissue as we have reported in experimental models of Huntington's disease and ALS, we tested the protein expression of MT1 in brain tissues of mouse pups. Along with melatonin-induced cell death in neonatal H-I mice in the short-term, we evaluated whether the expressions of MT1 are reduced in brains of pups at 12, 24 and 48 hr post H-I injury by Western blot analysis (FIG. 28A). Interestingly, we observed that MT1 is depleted in the brains of neonatal H-I mice and this reduction occurred in mice exposed to hypoxia alone (H) although with more reduction in mice exposed to H-I (FIG. 28A). As the contralateral brain hemisphere is also exposed to hypoxia, it is likely that the MT1 reduction in the contralateral side was caused by exposure to hypoxia (FIG. 28B, 28C). Furthermore, as is evident from FIG. 28A, there was a time-dependent graduated reduction of MT1 receptor in brain tissue in H-I pups compared to controls. The expression was maximally suppressed at 24 and 48 hr post hypoxia-ischemia (FIG. 28A-28C). However, melatonin significantly ameliorated MT1 loss by western blot analysis through upregulation of MT1 receptors in brains of melatonin treated H-I pups at 48 hr (FIG. 28C).

Figure 28D:
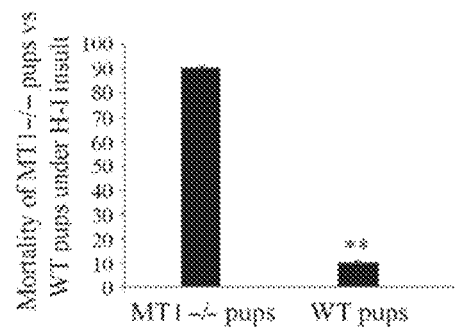

We previously reported that the knockdown of MT1 by siRNA sensitizes cultured striatal neurons to cell death.[14] To directly determine the importance of MT1 receptor in neonatal H-I brain injury, here we compared the hypoxia-ischemia induced mortality between MT1 knockout pups and C57BL6-wild type pups and found a remarkably increased mortality in MT1 −/− pups group (90.0%±4.1) compared to C57BL6-wild type pups (10.0%±4.1) (5 litter of MT1 −/− pups were compared with 5 litters of wild type pups). Our observations therefore demonstrated that mice lacking in MT1 receptors showed significantly increased mortality (FIG. 28D).

REFERENCES

1. Robertson C, Finer N. Term infants with hypoxic-ischemic encephalopathy: Outcome at 3.5 years. Dev Med Child Neurol. 1985; 27:473-484
2. McLean C, Ferriero D. Mechanisms of hypoxic-ischemic injury in the term infant. Semin Perinatol. 2004; 28:425-432
3. McDonald J W, Silverstein F S, Johnston M V. Mk-801 protects the neonatal brain from hypoxic-ischemic damage. Eur J Pharmacol. 1987; 140:359-361
4. Marret S, Mukendi R, Gadisseux J F, et al. Effect of ibotenate on brain development: An excitotoxic mouse model of microgyria and posthypoxic-like lesions. J Neuropathol Exp Neurol. 1995; 54:358-370
5. Signorini C, Ciccoli L, Leoncini S, et al. Free iron, total f-isoprostanes and total f-neuroprostanes in a model of neonatal hypoxic-ischemic encephalopathy: Neuroprotective effect of melatonin. J Pineal Res. 2009; 46:148-154
6. Holtzman D M, Sheldon R A, Jaffe W, et al. Nerve growth factor protects the neonatal brain against hypoxic-ischemic injury. Ann Neurol. 1996; 39:114-122
7. Muller M M, Middelanis J, Meier C, et al. 17beta-estradiol protects 7-day old rats from acute brain injury and reduces the number of apoptotic cells. Reprod Sci. 2013; 20:253-261
8. Thoresen M, Bagenholm R, Loberg E M, et al. Posthypoxic cooling of neonatal rats provides protection against brain injury. Arch Dis Childhood. Fetal Neonat Ed. 1996; 74:F3-9
9. Ma H, Sinha B, Pandya R S, et al. Therapeutic hypothermia as a neuroprotective strategy in neonatal hypoxic-ischemic brain injury and traumatic brain injury. Curr Mol Med. 2012; 12:1282-1296
10. Cotten C M, Shankaran S. Hypothermia for hypoxic-ischemic encephalopathy. Exp Rev Obstet & Gynec. 2010; 5:227-239
11. Zhang Y, Cook A, Kim J, et al. Melatonin inhibits the caspase-1/cytochrome c/caspase-3 cell death pathway, inhibits mt1 receptor loss and delays disease progression in a mouse model of amyotrophic lateral sclerosis. Neurobiol Dis, 2013; 55:26-35
12. Jacob S, Poeggeler B, Weishaupt J H, et al. Melatonin as a candidate compound for neuroprotection in amyotrophic lateral sclerosis (als): High tolerability of daily oral melatonin administration in als patients. J Pineal Res. 2002; 33:186-187
13. Weishaupt J H, Bartels C, Polking E, et al. Reduced oxidative damage in als by high-dose enteral melatonin treatment. J Pineal Res. 2006; 41:313-323
14. Wang X, Sirianni A, Pei Z, et al. The melatonin mt1 receptor axis modulates mutant huntingtin-mediated toxicity. J Neurosci. 2011; 31:14496-14507
15. Wang X, Zhu S, Pei Z, et al. Inhibitors of cytochrome c release with therapeutic potential for huntington's disease. J Neurosci. 2008; 28:9473-9485
16. Srinivasan V, Pandi-Perumal S R, Cardinali D P, et al. Melatonin in alzheimer's disease and other neurodegenerative disorders. Behav Brain Funct. 2006; 2:15
17. Cardinali D P, Furio A M, Brusco L I. Clinical aspects of melatonin intervention in Alzheimer's disease progression. Curr Neurophannacol. 2010; 8:218-227
18. Belaid H, Adrien J, Karachi C, Hirsch E C, Francois C. Effect of melatonin on sleep disorders in a monkey model of Parkinson's disease. Sleep Med. 2015; 16:1245-1251.
19. Lopez-Gonzalez A, Alvarez-Sanchez N, Lardone P J et al. Melatonin treatment improves primary progressive multiple sclerosis: a case report. J Pineal Res. 2015; 58:173-177
20. Wang X, Figueroa B E, Stavrovskaya I G, et al. Methazolamide and melatonin inhibit mitochondrial cytochrome c release and are neuroprotective in experimental models of ischemic injury. Stroke. 2009; 40:1877-1885
21. Kilic E, Kilic U, Yulug B, et al. Melatonin reduces disseminate neuronal death after mild focal ischemia in mice via inhibition of caspase-3 and is suitable as an add-on treatment to tissue-plasminogen activator. J Pineal Res. 2004; 36:171-176
22. Carloni S, Perrone S, Buonocore G, et al. Melatonin protects from the long-term consequences of a neonatal hypoxic-ischemic brain injury in rats. J Pineal Res. 2008; 44:157-164
23. Wong C S, Jow G M, Kaizaki A, et al. Melatonin ameliorates brain injury induced by systemic lipopolysaccharide in neonatal rats. Neuroscience. 2014; 267:147-156
24. Carloni S, Favrais G, Saliba E, et al. Melatonin modulates neonatal brain inflammation through endoplasmic reticulum stress, autophagy, and mir-34a/silent information regulator 1 pathway. J Pineal Res. 2016; 61:370-380

25. Robertson N J, Faulkner S, Fleiss B, et al. Melatonin augments hypothermic neuroprotection in a perinatal asphyxia model. Brain. 2013; 136:90-105
26. Alonso-Alconada D, Alvarez A, Arteaga 0, et al. Neuroprotective effect of melatonin: A novel therapy against perinatal hypoxia-ischemia. Int J Mol Sci. 2013; 14:9379-9395
27. Cetinkaya M, Alkan T, Ozyener F, et al. Possible neuroprotective effects of magnesium sulfate and melatonin as both pre- and post-treatment in a neonatal hypoxic-ischemic rat model. Neonatology. 2011; 99:302-310
28. Wang X. The antiapoptotic activity of melatonin in neurodegenerative diseases. CNS Neurosci Therap. 2009; 15:345-357
29. Wang X. The antiapoptotic effects of melatonin in neonatal hypoxic-ischemic brain injury and adult ischemic stroke. JSM Neurosurg Spine. 2014; 2:1033
30. Manchester L C, Coto-Montes A, Boga J A, et al. Melatonin: an ancient molecule that makes oxygen metabolically tolerable. J Pineal Res. 2015; 59:403-419
31. Reiter R J, Mayo J C, Tan D X, et al. Melatonin as an antioxidant: under promises but over delivers. J Pineal Res. 2016; 61:253-278.
32. Dubocovich M L, Markowska M. Functional mt1 and mt2 melatonin receptors in mammals. Endocrine. 2005; 27:101-110
33. Lacoste B, Angeloni D, Dominguez-Lopez S, et al. Anatomical and cellular localization of MT1 and MT2 receptors in the adult rat brain. J Pineal Res. 2015; 58:397-417.
34. Thomas L, Purvis C C, Drew J E, et al. Melatonin receptors in human fetal brain: 2-[(125)i]iodomelatonin binding and mtl gene expression. J Pineal Res. 2002; 33:218-224
35. Mahle C D, Watson A J. Melatonin receptors: Potential targets for central nervous system disorders. Exp Opin Investig Drugs. 1997; 6:399-406
36. Savaskan E, Ayoub M A, Ravid R, et al. Reduced hippocampal mt2 melatonin receptor expression in alzheimer's disease. J Pineal Res. 2005; 38:10-16
37. Adi N, Mash D C, Ali Y, et al. Melatonin mt1 and mt2 receptor expression in parkinson's disease. Med Sci Monit. 2010; 16:BR61-67
38. Wu Y H, Ursinus J, Zhou J N, et al. Alterations of melatonin receptors mtl and mt2 in the hypothalamic suprachiasmatic nucleus during depression. J Affect Disord. 2013; 148:357-367
39. Musshoff U, Riewenherm D, Berger E, et al. Melatonin receptors in rat hippocampus: Molecular and functional investigations. Hippocampus. 2002; 12:165-173
40. Rice J E 3rd, Vannucci R C, Brierley J B. The influence of immaturity on hypoxic-ischemic brain damage in the rat. Ann Neurol. 1981; 9:131-141
41. Schmued L C, Albertson C, Slikker W, Jr. Fluoro-jade: A novel fluorochrome for the sensitive and reliable histochemical localization of neuronal degeneration. Brain Res. 1997; 751:37-46
42. Wang S, Guan Y, Chen Y, et al. Role of wntl and fzdl in the spinal cord pathogenesis of amyotrophic lateral sclerosis-transgenic mice. Biotechnol Lett. 2013; 35:1199-1207
43. Zhou H, Wang J, Jiang J, et al. N-acetyl-serotonin offers neuroprotection through inhibiting mitochondrial de ath pathways and autophagic activation in experimental models of ischemic injury. J Neurosci. 2014; 34:2967-2978
44. Zhang Y, Wang X, Baranov S V, et al. Dipyrone inhibits neuronal cell death and diminishes hypoxic/ischemic brain injury. Neurosurgery. 2011; 69:942-956
45. Bartley J, Soltau T, Wimborne H, et al. Brdu-positive cells in the neonatal mouse hippocampus following hypoxic-ischemic brain injury. BMC Neurosci. 2005; 6:15
46. Martin M, Macias M, Escames G, et al. Melatonin but not vitamins C and E maintains glutathione homeostasis in t-butyl hydroperoxide-induced mitochondrial oxidative stress. FASEB J. 14:1677-1679
47. Young K W, Pinon L G, Bampton E T, et al. Different pathways lead to mitochondrial fragmentation during apoptotic and excitotoxic cell death in primary neurons. J Biochem Mol Toxicol. 2010; 24:335-341
48. Jahani-Asl A, Cheung E C, Neuspiel M, et al. Mitofusin 2 protects cerebellar granule neurons against injury-induced cell death. J Biol Chem. 2007; 282:23788-23798
49. Rossiter J P, Anderson L L, Yang F, et al. Caspase-3 activation and caspase-like protcolytic activity in human perinatal hypoxic-ischemic brain injury. Acta Neuropathol. 2002; 103:66-73
50. Han B H, D'Costa A, Back S A, et al. Bdnf blocks caspase-3 activation in neonatal hypoxia-ischemia. Neurobiol Dis. 2000; 7:38-53
51. Reiter R J, Calvo J R, Karbownik M, et al. Melatonin and its relation to the immune system and inflammation. Ann NY Acad Sci. 2000; 917:376-386
52. Lin C, Chao H, Li Z, et al. Melatonin attenuates traumatic brain injury-induced inflammation: a possible role of mitophagy. J Pineal Res. 2016; 61:177-186.
53. Welin A K, Svedin P, Lapatto R, et al. Melatonin reduces inflammation and cell death in white matter in the midgestation fetal sheep following umbilical cord occlusion. Ped Res. 2007; 61:153-158
54. Dubocovich M L, Delagrange P, Krause D N, et al. International union of basic and clinical pharmacology. Lxxv. Nomenclature, classification, and pharmacology of g protein-coupled melatonin receptors. Pharmacol Rev. 2010; 62:343-380
55. Husson I, Mesples B, Bac P, et al. Melatoninergic neuroprotection of the murine periventricular white matter against neonatal excitotoxic challenge. Ann Neurol. 2002; 51:82-92
56. Morgan P J, Barrett P, Howell H E, et al. Melatonin receptors: Localization, molecular pharmacology and physiological significance. Neurochem Int. 1994; 24:101-146
57. Chen Y, Tjong Y W, Ip S F, et al. Melatonin enhances the hypoxic response of rat carotid body chemoreceptor. J Pineal Res. 2005; 38:157-163
58. Kilic U, Yilmaz B, Ugur M, et al., Evidence that membrane-bound G protein-coupled melatonin receptors MT1 and MT2 are not involved in the neuroprotective effects of melatonin in focal cerebral ischemia. J Pineal Res. 2012; 52:228-235
59. Lee C H, Yoo K Y, Choi J H, et al. Melatonin's protective action against ischemic neuronal damage is associated with up-regulation of the MT2 melatonin receptor. J Neurosci Res. 2010; 88:2630-2640
60. Chern C M, Liao J F, Wang Y H, Shen Y C. Melatonin ameliorates neural function by promoting endogenous neurogenesis through the MT2 melatonin receptor in ischemic-stroke mice. Free Radic Biol Med. 2012; 52:1634-1647

61. Olegario J G, Silva M V, Machado J R, et al. Pulmonary innate immune response and melatonin receptors in the perinatal stress. Clin Dev Immunol. 2013; 2013:340959
62. Correa R R, Barrilari S E, Guimaraes C S, et al. Expression of the melatonin receptor and tryptophan hydroxylase in placentas of the fetus with intra-uterine stress. Eur J Obstet Gynecol Reprod Biol. 2009; 147:234-236
63. Parada E, Buendia I, Leon R, et al. Neuroprotective effect of melatonin against ischemia is partially mediated by alpha-7 nicotinic receptor modulation and ho-1 over-expression. J Pineal Res. 2014; 56:204-212
64. Manev H, Uz T, Kharlamov A, et al. Increased brain damage after stroke or excitotoxic seizures in melatonin-deficient rats. FASEB J. 1996; 10:1546-1551
65. Weil Z M, Hotchkiss A K, Gatien M L, et al. Melatonin receptor (mt1) knockout mice display depression-like behaviors and deficits in sensorimotor gating. Brain Res Bull.
2006; 68:425-429
66. Peters J L, Earnest B J, Tjalkens R B, et al. Modulation of intercellular calcium signaling by melatonin in avian and mammalian astrocytes is brain region-specific. J Compar Neurol. 2005; 493:370-380
67. Stanimirovic D B, Ball R, Durkin J P. Stimulation of glutamate uptake and Na,K-ATPase activity in rat astrocytes exposed to ischemia-like insults. Glia. 1997; 19:123-134
68. Swanson R A, Farrell K, Stein B A. Astrocyte energetics, function, and death under conditions of incomplete ischemia: A mechanism of glial death in the penumbra. Glia. 1997; 21:142-153
69. Pei Z, Fung P C, Cheung R T. Melatonin reduces nitric oxide level during ischemia but not blood-brain barrier breakdown during reperfusion in a rat middle cerebral artery occlusion stroke model. J Pineal Res. 2003; 34:110-118
70. Andrabi S A, Sayeed I, Siemen D, et al. Direct inhibition of the mitochondrial permeability transition pore: A possible mechanism responsible for anti-apoptotic effects of melatonin. FASEB J. 2004; 18:869-871
71. Wu Q, Chen W, Sinha B, et al. Neuroprotective agents for neonatal hypoxic-ischemic brain injury. Drug Dis Today. 2015; 20:1372-1381
72. Fulia F, Gino E, Cuzzocrea S, et al. Increased levels of malondialdehyde and nitrite/nitrate in the blood of asphyxiated newborns. J Pineal Res. 2001; 31:343-349.
73. Gino E, Pellegrino S, Gino P, et al. Oxidative stress of the newborn in the pre- and postnatal period and the clinical utility of melatonin. J Pineal Res. 2009; 46:128-139.
74. Aly H, Elmandy H, El-Dib M, et al. Melatonin use for neuroprotection in perinatal asphyxia: A randomized controlled pilot study. J Perinatol. 2015; 35:186-191
75. Cheung R T, Tipoe G L, Tam S, et al. Preclinical evaluation of pharmacokinetics and safety of melatonin in propylene glycol for intravenous administration. J Pineal Res. 2006; 41:337-343

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing and treating a newborn subject who is suspected of having hypoxic-ischemic encephalopathy (HIE), the method comprising:
   providing a sample comprising urine from the subject;
   determining a level of one or more melatonin pathway agents selected from the group consisting of melatonin, tryptophan, 5-hydroxytryptophan (5-HTP), serotonin, and melatonin receptor 1A (MT1) in the sample;
   identifying a subject who has a level of the agent below a reference level; and
   administering a treatment for HIE to the subject.
2. The method of claim 1, wherein the treatment comprises administration of one or more agents selected from the group consisting of melatonin, 5-HTP, serotonin, and NAS.
3. The method of claim 2, wherein the treatment comprises administration of melatonin or NAS.
4. The method of claim 1, wherein the treatment comprises administration of hypothermia.
5. The method of claim 3, comprising determining a level of one or more melatonin pathway agents selected from the group consisting of tryptophan, melatonin, 5-HTP, serotonin, and MT1 in the sample.
6. The method of claim 1, wherein the subject is a newborn, and the sample is obtained from the newborn subject within 2-24, or 12-24 hours of birth.
7. The method of claim 1, wherein the subject does not have sleep disturbance.
8. The method of claim 1, comprising determining a level of melatonin in the sample.
9. The method of claim 1, comprising determining a level of tryptophan in the sample.
10. The method of claim 1, comprising determining a level of 5-HTP in the sample.
11. The method of claim 1, comprising determining a level of serotonin in the sample.
12. The method of claim 1, comprising determining a level of MT1 in the sample.

* * * * *